(12) United States Patent
Gautier et al.

(10) Patent No.: US 11,457,653 B2
(45) Date of Patent: Oct. 4, 2022

(54) CREAM SUBSTITUTE COMPRISING PULSE PROTEIN

(71) Applicant: Cosucra Groupe Warcoing S.A., Warcoing (BE)

(72) Inventors: Gaelle Gautier, Mons-en-Baroeul (FR); Pauline Beguin, Cuesmes (BE); Christophe Vervacke, Rumillies (BE); Julie Pihen, Leers (FR)

(73) Assignee: Cosucra Groupe Warcoing S.A., Warcoing (BE)

( * ) Notice: Subject to any disclaimer, the term of this patent is extended or adjusted under 35 U.S.C. 154(b) by 0 days.

(21) Appl. No.: 16/764,445

(22) PCT Filed: Nov. 28, 2018

(86) PCT No.: PCT/EP2018/082761
§ 371 (c)(1),
(2) Date: May 15, 2020

(87) PCT Pub. No.: WO2019/105961
PCT Pub. Date: Jun. 6, 2019

(65) Prior Publication Data
US 2020/0359665 A1 Nov. 19, 2020

(30) Foreign Application Priority Data

Nov. 28, 2017 (EP) ..................................... 17204213

(51) Int. Cl.
*A23L 9/20* (2016.01)
*A23L 29/269* (2016.01)
(Continued)

(52) U.S. Cl.
CPC .............. *A23L 9/24* (2016.08); *A23C 11/103* (2013.01); *A23G 9/38* (2013.01); *A23G 9/42* (2013.01);
(Continued)

(58) Field of Classification Search
CPC ........ A23L 9/24; A23L 29/273; A23L 29/244; A23L 33/185; A23C 11/103; A23G 9/38; A23G 9/42
(Continued)

(56) References Cited

U.S. PATENT DOCUMENTS 4,411,926 A 10/1983 Trumbetas et al.
2010/0063254 A1 3/2010 Lotz et al.
(Continued)

FOREIGN PATENT DOCUMENTS

JP 2010-507597 A 3/2010
JP 2012-519011 A 8/2012
(Continued)

OTHER PUBLICATIONS

Translation of WO-2010100370-A1 (Year: 2010).*
(Continued)

*Primary Examiner* — Brent T O'Hern
(74) *Attorney, Agent, or Firm* — Amster, Rothstein & Ebenstein LLP

(57) ABSTRACT

The present invention is situated in the field of food technology. The invention more specifically relates to a cream substitute wherein the milk or dairy-derived components, e.g. the milk protein component has been replaced by intact pulse protein. The invention further provides cream substitute products such as whipped cream, culinary cream, ice cream and milk dessert substitute as well as methods for producing these.

15 Claims, 9 Drawing Sheets

(51) Int. Cl.
*A23L 29/244* (2016.01)
*A23L 33/185* (2016.01)
*A23C 11/10* (2021.01)
*A23G 9/38* (2006.01)
*A23G 9/42* (2006.01)

(52) U.S. Cl.
CPC ........... *A23L 29/244* (2016.08); *A23L 29/273* (2016.08); *A23L 33/185* (2016.08)

(58) Field of Classification Search
USPC .......................................................... 426/572
See application file for complete search history.

(56) References Cited

U.S. PATENT DOCUMENTS

| | | | |
|---|---|---|---|
| 2011/0311599 A1* | 12/2011 | Boursier | A23L 29/35 424/401 |
| 2015/0104556 A1* | 4/2015 | Kumar | A23C 13/125 426/565 |
| 2018/0360070 A1 | 12/2018 | McIntosh | |
| 2019/0021387 A1 | 1/2019 | Freres | |

FOREIGN PATENT DOCUMENTS

| | | | | |
|---|---|---|---|---|
| WO | WO-2010100370 A1 * | 9/2010 | | A23C 11/103 |
| WO | 2017/129921 A1 | 8/2017 | | |
| WO | 2017/132707 A1 | 8/2017 | | |
| WO | 2017132707 A1 | 8/2017 | | |
| WO | 2017153669 A1 | 9/2017 | | |

OTHER PUBLICATIONS

International Search Report dated Feb. 19, 2019 from PCT International Patent Application No. PCT/EP2018/082761.

Written Opinion dated Feb. 19, 2019 from PCT International Patent Application No. PCT/EP2018/082761.

Chan et al., "A Non-Dairy Frozen Dessert Utilizing Pea Protein Isolate and Hydrogenated Canola Oil," Food Technology, vol. 46, No. 1, Jan. 1992, pp. 88-92.

"CocoWhip! Coconut Whipped Topping," Mintel, Database GNPD [online], database accession No. 2918415, Jan. 2015, 4 pages.

Rutherfurd, "Methodology for Determining Degree of Hydrolysis of Proteins in Hydrolysates: A Review," Journal of AOAC International, vol. 93. No. 5, Sep. 1, 2010, pp. 1515-1522.

Adler-Nissen, "Determination of the Degree of Hydrolysis of Food Protein Hydrolysates by Trinitrobenzenesulfonic Acid," J. Agric. Food Chem., vol. 27, No. 6, 1979, pp. 1256-1262.

Japan Patent Office, "Notice of Reasons for Reufal," issued in Japanese Patent Application No. 2020-529140, which is a counterpart of U.S. Appl. No. 16/764,445, dated Jul. 25, 2020, 16 pages (9 pages of English Translation of Office Action and 7 pages of original Office Action).

* cited by examiner

CREAM SUBSTITUTE COMPRISING PULSE PROTEIN

CROSS-REFERENCE TO RELATED APPLICATIONS

This application is a U.S. national stage entry under 35 U.S.C. § 371 of PCT International Patent Application No. PCT/EP2018/082761, filed Nov. 28, 2018, which claims priority to European Patent Application No. 17204213.7, filed Nov. 28, 2017, the contents of each of which are incorporated herein by reference in their entirety.

FIELD OF THE INVENTION

The present invention is situated in the field of food technology. The invention more specifically relates to a cream substitute wherein the milk or dairy-derived components, e.g. the milk protein component has been replaced by intact pulse protein. The invention further provides cream substitute products such as whipped cream, culinary cream, ice cream and milk dessert as well as methods for producing these.

BACKGROUND OF THE INVENTION

Cream is the fatty part of milk, which rises to the surface when the liquid is allowed to stand unless homogenized. In many countries, cream is sold in several grades depending on the total butterfat content. Cream can be dried to a powder for shipment to distant markets. Cream has high levels of saturated fat. Cream is used as an ingredient in many foods, including ice cream, whipped cream, milk dessert, as it is, many sauces, soups, stews, puddings, and some custard bases, and it is also used in making cakes. Different type of cream exists like raw fresh cream, fleurette cream, double cream, half cream or coffee cream, whole cream, liquid fresh cream, liquid fresh light cream, liquid sterilized cream or UHT cream.

The "whipped cream" is whipped by incorporation of air. The whipped cream is, in general, made with liquid cream, or fleurette cream 35% fat, UHT or sterilized. The whipped cream contains 75% cream or light cream, which can be sweet (up to maximum 15% sugars of its composition) and may contain lactic ferments, natural flavours, stabilizers, or milk proteins. Chantilly cream is therefore a type of "whipped cream" (without lactic ferments) that must contain at least 30% fat, and be sweetened to at least 15% sugars. Whipped cream is for example served as a topping on ice cream sundaes, milkshakes, lassi, eggnog and sweet pies.

Milk dessert comprise milk, sweet or flavoured and may contain lactic ferments. Some examples are listed hereafter: flavoured gummy milks, gummed milks with whipped cream, dessert creams, foams and the like, crème-brulee, floating islands, rice cakes, semolina cakes, eggs with milk, egg flans, caramel creams, rice pudding, egg creams and yoghurt.

Ice cream is a frozen mixture of a combination of components of milk, sweeteners, stabilizers, emulsifiers and flavouring. Other ingredients such as egg products, colourings, and starch hydrolysates may be added also. This mixture (called a mix) is pasteurized and homogenized before freezing. Some of the characteristics that merit consideration are cost, handling properties (including mix viscosity, freezing point, and overrun of the mix), flavour, body and texture, food value, colour, and general palatability of the finished product.

Milk is one of the most common food allergens. People with an allergy to cow's milk may also be allergic to milk from other animals, including sheep and goats. Within a short period of time after consuming milk or a milk protein, they may experience the following symptoms: hives, stomach upset, vomiting, bloody stools, especially in infants, and in some extreme cases anaphylaxis, which is a rare, potentially life-threatening reaction that impairs breathing and can send the body into shock.

Some milk alternatives already exist like: almond-, coconut-, rice-, oat- or soy-based products but some of these alternatives are listed as common allergens or their nutritional values are not always satisfying.

In view of all the disadvantages at the health, economic, environmental and nutritional level that are associated with the consumption of dairy products and dairy alternatives already in the market, there is still a need to find a good alternative cream substitute, to dairy-based cream.

SUMMARY OF THE INVENTION

It is the merit of the applicant of having discovered that pulse protein, preferably pea protein, could surprisingly and advantageously replace milk protein in cream substitutes which are useable as culinary cream, whipped cream, ice cream and milk dessert substitute, while maintaining organoleptic properties, and in particular obtaining gustatory, olfactory, visual and tactile properties that are at least equivalent, or even better than those made with milk proteins or other vegetable non-pulse proteins as main proteins in the cream. Particular advantages of pulse proteins are that they are not allergenic and are low cost compared to milk proteins and other vegetable proteins.

According to a main aspect of the present invention, a cream substitute comprising pulse protein as the main protein component is described.

In particular, the present invention is further captured by any one or any combination of one or more of the below numbered specific aspects:

1. A cream substitute comprising non-hydrolysed pulse protein in an amount comprised between 0.5 wt. % and 10 wt. %, preferably between 1 wt. % and 8 wt. %, such as between 1 wt. % and 5 wt. %, more preferably between 1.2 wt. % and 4.5 wt. %, based on the total weight of the cream substitute and wherein the degree of hydrolysis of the pulse protein is less than 5%, preferably less than 4%, more preferably less than 3%, and wherein said cream substitute contains less than 1 wt. %, preferably less than 0.5 wt. % of dairy-derived ingredients based on the total weight of the cream substitute.
2. The cream substitute according to aspect 1, wherein the cream substitute comprises pulse protein derived from pulses selected from the group comprising lentils, beans, such as *faba* beans, peas, chickpeas and combinations thereof.
3. The cream substitute according to aspect 1 or 2, additionally comprising a soluble fiber in an amount between 0.5 wt. % and 5 wt. %, preferably between 2 wt. % and 4 wt. %, based on the total weight of the cream substitute, preferably wherein said soluble fiber is selected from inulin, gluco-oligosaccharides (GOSs), iso-malto-oligosaccharides (IMOs), galacto-oligosaccharides (TOSs), pyrodextrins, polydextrose, branched maltodextrins, indigestible dextrins and soluble oligosaccharides derived from oleaginous plants or protein-producing plants, or combinations thereof.

4. The cream substitute according to any of aspects 1 to 3, wherein said pulse protein is the main protein present in the cream substitute and wherein said cream substitute may comprise other proteins selected from caseinate, casein, whey, soy, oat, coconut, rice, gluten, nut, wheat and almonds, and wherein the total amount of non-pulse protein is lower than the amount of pulse protein.

5. The cream substitute according to any one of aspects 1 to 3, wherein the pulse protein is the sole source of vegetable protein, preferably wherein the pulse protein is the sole source of protein.

6. The cream substitute according to any one of aspects 1 to 5, wherein the pulse protein is pea protein, more preferably a pea protein isolate.

7. The cream substitute according to any one of aspects 1 to 5, wherein the pulse protein is *faba* bean protein, more preferable a *faba* bean protein isolate.

8. A cream substitute according to any one of aspects 1 to 7 wherein said cream substitute is chosen from: ice cream, whipped cream, culinary cream, or a milk dessert product, preferably a milk dessert product made without lactic ferments.

9. A cream substitute comprising:
   non-hydrolysed pulse protein in an amount comprised between 0.5 wt. % and 10 wt. %, preferably between 1 wt. % and 8 wt. %, such as between 1 wt. % and 5 wt. %, more preferably between 1.2 wt. % and 4.5 wt. %, wherein the degree of hydrolysis of the pulse protein is less than 5%, preferably less than 4%, more preferably less than 3%
   a soluble fiber in an amount comprised between 0.5 wt. % and 5 wt. %, and
   at least one further protein selected from caseinate, casein, whey, soy, oat, coconut, rice, gluten, nut, wheat and almonds, and wherein the total amount of proteins, other than pulse protein, is lower than the mount of pulse protein,
   wherein said cream substitute contains less than 1 wt. %, preferably less than 0.5 wt. % of dairy-derived ingredients, and wherein said wt. % are calculated based on the total weight of the cream substitute.

10. An ice cream according to aspect 8 comprising:
    non-hydrolysed pulse protein in an amount comprised between 0.5 wt. % and 10 wt. %, preferably between 1 wt. % and 8 wt. %, such as between 1 wt. % and 5 wt. %, more preferably between 1.2 wt. % and 4.5 wt. %, wherein the degree of hydrolysis of the pulse protein is less than 5%, preferably less than 4%, more preferably less than 3%,
    a soluble fiber in an amount comprised between 0.5 wt. % and 5 wt. %, preferably between 2 wt. % and 4 wt. %,
    sugar in an amount of from 0 wt. % to 20 wt. %,
    glucose and/or dextrose and/or fructose in an amount of from 0 wt. % to 20 wt. %,
    vegetable fat in an amount of from 1.5 wt. % to 5 wt. %, and optionally
    additives selected from: flavours, colorants, stabilisers, thickeners, gelling agents, emulsifiers, bulking agent in an amount of from 0.05 wt. % to 10 wt. %, and wherein said wt. % are calculated based on the total weight of the ice cream.

11. An ice cream according to aspect 10 wherein the amount of non-hydrolysed pulse protein is between 1.0 wt. % and 5.0 wt. %, such as between 0.8 wt. % and 4.5 wt. %.

12. A culinary cream according to aspect 8 comprising:
    non-hydrolysed pulse protein in an amount comprised between 0.5 wt. % and 10 wt. %, preferably between 1 wt. % and 8 wt. %, such as between 1 wt. % and 5 wt. %, more preferably between 1.2 wt. % and 4.5 wt. %, wherein the degree of hydrolysis of the pulse protein is less than 5%, preferably less than 4%, more preferably less than 3%,
    fructose and/or glucose and/or saccharose in an amount from 0 wt. % to 4 wt. %,
    vegetable oil in an amount from 0 wt. % to 20 wt. %, and optionally
    additives selected from flavours, colorants, stabilisers, thickeners, gelling agents, emulsifiers, bulking agent in an amount from 0.05 wt. % to 10 wt. %, and wherein said wt. % are calculated based on the total weight of the culinary cream.

13. A culinary cream according to aspect 12 wherein the amount of non-hydrolysed pulse protein is between 1.0 wt. % and 5.0 wt. %, such as between 0.84 wt. % and 4.5 wt. %.

14. A milk dessert product according to aspect 8 comprising:
    non-hydrolysed pulse protein in an amount comprised between 0.5 wt. % and 10 wt. %, preferably between 1 wt. % and 8 wt. %, such as between 1 wt. % and 5 wt. %, more preferably between 1.2 wt. % and 4.5 wt. %, wherein the degree of hydrolysis of the pulse protein is less than 5%, preferably less than 4%, more preferably less than 3%,
    sugar in an amount from 7 wt. % to 15 wt. %,
    starch in an amount from 0 wt. % to 5 wt. %,
    vegetable fat in an amount from 0 wt. % to 5 wt. %, and optionally
    additives selected from: flavours, colorants, stabilisers, thickeners, gelling agents, emulsifiers, sweetener, bulking agent in an amount from 0.05 wt. % to 5 wt. %; and wherein said wt. % are calculated based on the total weight of the milk dessert.

15. A milk dessert product according to aspect 14 wherein the amount of non-hydrolysed pulse protein is between 1.0 wt. % and 10.0 wt. %, such as between 3.28 wt. % and 9 wt. %, or between 1.0 wt. % and 5.0 wt. %.

16. A whipped cream according to aspect 8 comprising:
    non-hydrolysed pulse protein in an amount comprised between 0.5 wt. % and 10 wt. %, preferably between 1 wt. % and 8 wt. %, such as between 1 wt. % and 5 wt. %, more preferably between 1.2 wt. % and 4.5 wt. %, wherein the degree of hydrolysis of the pulse protein is less than 5%, preferably less than 4%, more preferably less than 3%,
    sugar in an amount of from 0 wt. % to 15 wt. %,
    vegetable oil in an amount of from 15 wt. % to 30 wt %, and optionally
    additives selected from: flavours, colorants, stabilisers, thickeners, gelling agents, emulsifiers, bulking agent, sweeteners in an amount of from 0.05 wt. % to 2 wt. %; and wherein said wt. % are calculated based on the total weight of the whipped cream.

17. A whipped cream according to aspect 16 wherein the amount of non-hydrolysed pulse protein is between 1.0 wt. % and 5.0 wt. %, such as between 0.84 wt. % and 2.7 wt. %.

DETAILED DESCRIPTION

Figure 1:
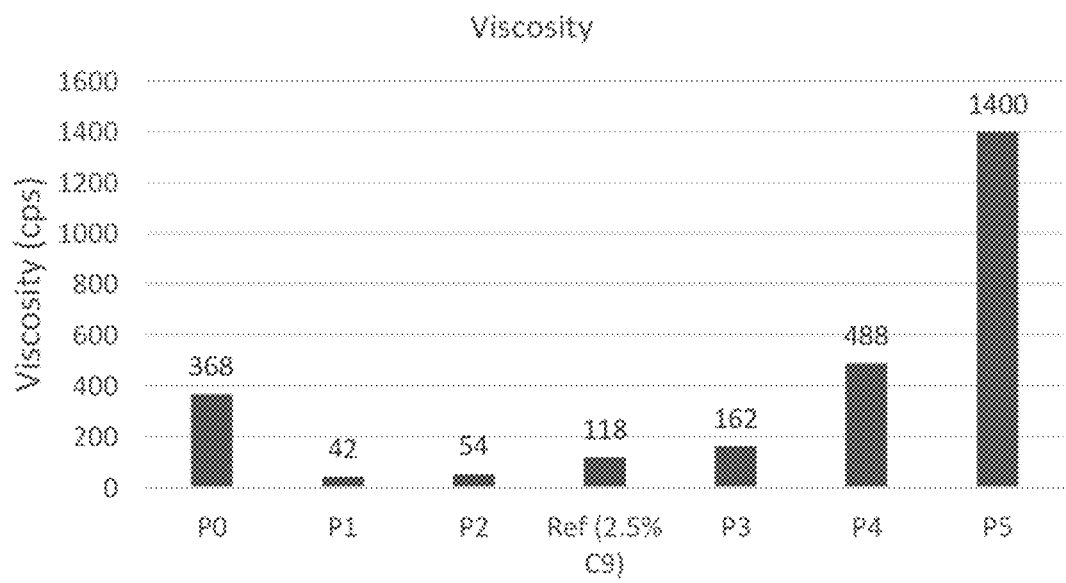
FIG. 1 represents the viscosity of the liquid cream containing 1%, 2%, 2.5%, 3%, 4% and 5% Pisane™ C9 or without Pisane™ C9 (P0).

Before the present method of the invention is described, it is to be understood that this invention is not limited to particular methods, components, products or combinations described, as such methods, components, products and combinations may, of course, vary. It is also to be understood that the terminology used herein is not intended to be limiting, since the scope of the present invention will be limited only by the appended claims.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. It will be appreciated that the terms "comprising", "comprises" and "comprised of" as used herein comprise the terms "consisting of", "consists" and "consists of", as well as the terms "consisting essentially of", "consists essentially" and "consists essentially of".

The recitation of numerical ranges by endpoints includes all numbers and fractions subsumed within the respective ranges, as well as the recited endpoints.

The term "about" or "approximately" as used herein when referring to a measurable value such as a parameter, an amount, a temporal duration, and the like, is meant to encompass variations of +/−20% or less, preferably +/−10% or less, more preferably +/−5% or less, and still more preferably +/−1% or less of and from the specified value, insofar such variations are appropriate to perform in the disclosed invention. It is to be understood that the value to which the modifier "about" or "approximately" refers is itself also specifically, and preferably, disclosed.

Whereas the terms "one or more" or "at least one", such as one or more or at least one member(s) of a group of members, is clear per se, by means of further exemplification, the term encompasses inter alia a reference to any one of said members, or to any two or more of said members, such as, e.g., any or etc. of said members, and up to all said members.

All references cited in the present specification are hereby incorporated by reference in their entirety. In particular, the teachings of all references herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may relate to several earlier described embodiments as variants thereof. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

The following detailed description, therefore, is not to be taken in a limiting sense, and the scope of the present invention is defined by the appended claims.

Pulses are the dried seeds of legumes. The four most common pulses are beans, chickpeas, lentils and peas. Lentils, as *Lens Culinaris*, are represented by: Beluga Lentils, Brown Lentils, French Green Lentils, Green Lentils and Red Lentils. Beans, as *Phaseolus Vulgaris*, are represented by: Adzuki Beans, Anasazi Beans, Appaloosa Beans, Baby Lima Beans, Black Calypso Beans, Black Turtle Beans, Dark Red Kidney Beans, Great Northern Beans, Jacob's Cattle Trout Beans, Large *Faba* Beans, Large Lima Beans, Mung Beans, Pink Beans, Pinto Beans, Romano Beans, Scarlet Runner Beans, Tongue of Fire, White Kidney Beans and White Navy Beans. Peas are represented by: Black-Eyed Peas, Green Peas, Marrowfat Peas, Pigeon Peas, Yellow Peas and Yellow-Eyed Peas. Chickpeas, as *Cicer Arietinum*, are represented by: Chickpea and Kabuli.

In a preferred embodiment, pea protein is used. Dry peas contain 20-30% lysine rich proteins. Pea proteins are mainly storage protein comprised of albumins and two globulins, legumin and vicilin which proteins may relatively easily solubilized and isolated. In addition, these proteins are characterized by high lysine content, which is deficient in many other proteins of plant origin. Solubility profile of pea protein isolates is similar to other legume proteins and is characterized by high solubility at alkaline pH-s, a minimum solubility at isoelectric point and moderate solubility in acidic medium. They are characterized by a relatively good emulsifying activity.

Pea protein can be prepared in three forms: pea flour, pea protein concentrate, and pea protein isolate. Pea flour is produced by dry milling of dehulled peas. Pea protein concentrate can be produced through the acid leaching procedure traditionally used to produce soy protein concentrates, but it is more economical to use dry separation methods. Pea protein isolate is produced by wet processing methods.

Proteins and starches within non-oilseed legumes such as peas can be efficiently fractionated by dry milling and air classification. Fine grinding results in flours containing populations of particles differentiated by size and density. Air classification of such flours separates the protein (fine fraction) from the starch (coarse fraction). In this dry process, whole or dehulled peas are pin milled to a very fine flour. During milling starch granules remain relatively intact, while the protein matrix is broken down into fine particles. Care must be used in milling to avoid damage to starch granules. The flour is air classified in a spiral air stream into a fine fraction containing approximately 75% of the total protein, but only 25% of the total mass; and a coarse fraction, containing most of the starch granules. The starch and protein fractions are separated in the air classifier based on their differential mass and size. The coarse fraction can be centrifugally separated from the fine fraction and carried into a coarse fraction duct. The fine fraction is carried with the air into the air cyclone. After milling, some protein bodies still adhere to the starch granules and some starch is still imbedded in the protein matrix. The level of adhering protein bodies and agglomerated starch and protein can be reduced by repeated pin milling and air classification. With such a double pass process, a yield of 33-35% total protein fraction (protein content of 56%, dry basis, N×6.25) was obtained for peas with an original protein content of about 25%.

Highly concentrated protein fractions (protein isolates) and protein concentrates from pea can be prepared by wet processing. The protein separation has been mainly based on solubilization of protein followed by isoelectric precipitation for subsequent recovery.

The isoelectric precipitation process for protein isolate production involves milling of the peas, followed by solubilization of the proteins in water, alkali, or acid; then centrifuging to remove the insoluble components. The solubilized proteins are then precipitated at their isoelectric pH. The precipitated protein curd is collected by centrifugation or sieving. The curd is dried as such to yield isoelectric protein isolate or neutralized and dried to yield a cationic-protein isolate.

Protein isolates have a total protein content (expressed in N 6.25) of at least 70% based on the dry matter, at least 75%, at least 80%, at least 85%, at least 90%, for example between 70% and 99%, preferably between 80% and 95%, more preferably between 80% and 90%. In a preferred embodiment, pea protein isolate is used. Pea protein isolates are commercially available. For instance Pisane™ is a range of pea protein isolates extracted from the yellow pea and is a commercially available product from Cosucra Groupe Warcoing (BE). The Pisane™ products comprise about 80 to 90% pea protein on a dry matter base (DM). In preferred embodiments, pea protein for use in the present invention is Pisane™ C9, obtained from Cosucra. Pisane™ C9 typically comprises from 84 to 88% pea protein based on dry weight of the isolate. Given that the isolate has a dry matter content of At least 93%, this corresponds to an actual pea protein content of between at least 78.12 and at least 81.84 percentage by weight of the isolate generally accepted is an amount of about 80 to 83 wt. %. Another source of pea protein isolate is Nutralys® S85F commercially available from Roquette Freres (FR).

According to another embodiment, another source of pulse protein isolate can be used, for instance derived from *Faba* bean protein isolates.

According to one preferred embodiment of the present invention, the cream substitute comprises at least one soluble vegetable fiber.

Preferably, said soluble fiber of vegetable origin is chosen from the group consisting of fructans, including inulin, glucooligosaccharides (GOSs), isomaltooligosaccharides (IMOs), galactooligosaccharides (TOSs), pyrodextrins, polydextrose, branched maltodextrins, indigestible dextrins and soluble oligosaccharides derived from oleaginous plants or protein-producing plants.

As used herein, the term "inulin" refers to a mixture of oligo- and/or polysaccharides of fructose which may have a terminal glucose. Inulins belong to a class of fibers known as fructans. In an embodiment, inulin can be represented, depending from the terminal carbohydrate unit, by the general formulae GFn and/or Fm, wherein G represents a glucose unit, F represents a fructose unit, n is an integer representing the number of fructose units linked to the terminal glucose unit, and m is an integer representing the number of fructose units linked to each other in the carbohydrate chain, preferably wherein n is at least 2, and m is at least 2. Inulins for use in the present invention encompass inulins with a terminal glucose which are also referred as alpha-Dglucopyranosyl-[beta-D-fructofuranosylyl]n−1)-D-fructofuranosides, as well as inulins without glucose which are also referred as beta-D-fructopyranosyl-p-fructofuranosylynl)-D-fructofuranosides. Inulins for use in the present invention can also encompass branched inulin. Inulins for use in the present invention can also encompass the hydrolysis products of inulins such as fructo-oligosaccharides (FOS), also called oligofructoses, which are fructose oligomers with a DP of 20, and they can also encompass fructo-oligosaccharides ending with a terminal glucose with a DP of 3-5 synthesized from sucrose. Preferably said fructo-oligosaccharides have an average DP by number of at least 3 and at most 7. Suitable saccharide chains of inulin from plant origin for use in the invention can have a DP ranging from 2 to about 100. Inulin can be a liquid or a powder product.

The use of a soluble fiber in the cream substitute may be used as a source of fiber, for nutritional value or in order to improve the quality of the cream substitute in term of firmness, stability or creamy texture.

The cream substitute may be in liquid form or in powder form. The cream substitute can be in the form of an ice cream, a whipped cream, a culinary cream, or a milk dessert substitute, preferably a milk dessert substitute made without lactic ferments.

Other Components:

The cream substitute may comprise at least one protein and at least one fat and/or one carbohydrate.

Fat component, may be in liquid or solid form, and may for example include: animal fats (butter, lard, tallow, chicken fat, and fish oils), cocoa butter and cocoa butter alternatives, lauric oils (coconut, palm kernel), olive oil, palm oil, rapeseed (canola) oil, soybean oil, sunflower seed oil, other vegetable oils or single cell oils; hydrogenated or not; and combinations thereof.

Carbohydrate component, may be in liquid or solid form, and may for example: starch and maltodextrin from corn, tapioca, wheat or pea, glucose, fructose, saccharose, mono- and disaccharide.

Protein component, liquid or solid form, may be for example, casein, caseinate, whey, soy, oat, coconut, rice, gluten, nut, wheat and almonds, in addition to pulse protein.

Additives components such as flavours, colorants, stabilisers, thickeners, gelling agents, emulsifiers, bulking agent and sweeteners may also be found in the cream substitute.

As used herein, a "non-hydrolysed" protein is equivalent to an "intact" protein, meaning that the protein has not been subjected to a hydrolysis process. However, minor amounts of hydrolysed proteins may be present in the source of non-hydrolysed proteins, or may be added to the formulation, such as additional amino acids, such as, for example leucine, isoleucine, glutamine, arginine, or dipeptides and the like. According to another embodiment, intact protein may only possess a degree of hydrolysis (DH) of 5% or lower, preferably 4%, 3%, 2%, 1.9%, 1.8%, 1.7%, 1.6%, 1.5%, 1.4%, 1.3%, 1.2%, 1.1%, 1% or lower. According to another embodiment, the degree of hydrolysis of the pulse proteins is less than 2%.

As used herein, the term "dairy-free" encompasses products that are substantially free of all dairy-derived ingredients. Preferably the term covers products wherein no dairy-derived ingredients are actively added during processing or preparation and hence merely trace amounts of dairy-derived ingredients are present within the products. Typically, the cream substitute will contain less than about 1 wt. %, such as less than 0.9 wt. %, 0.8 wt. %, 0.7 wt. %, 0.6 wt. %, 0.5 wt. %, 0.4 wt. %, 0.3 wt. %, 0.2 wt. %, 0.1 wt. % or less of dairy-derived ingredients.

In a first aspect of the present invention, the cream substitute comprises intact (non-hydrolysed) pulse protein in an amount comprised between 0.5 wt. % and 10 wt. %, or between 0.42 wt. % and 9 wt. %, based on the total weight of the cream substitute, at least 0.5 wt. %, at least 0.6 wt. %, at least 0.7 wt. %, at least 0.8 wt. %, at least 0.9 wt. %, at least 1.0 wt. %, at least 1.1 wt. %, at least 1.2 wt. %, at least 1.3 wt. %, at least 1.4 wt. %, at least 1.5 wt. %, at least 1.6 wt. %, at least 1.7 wt. %, at least 1.8 wt. %, at least 1.9 wt. %, at least 2.0 wt. %, at least 2.1 wt. %, at least 2.2 wt. %, at least 2.3 wt. %, at least 2.4 wt. %, at least 2.5 wt. %, at least 2.6 wt. %, at least 2.7 wt. %, at least 2.8 wt. %, at least 2.9 wt. %, at least 3.0 wt. %, at least 3.1 wt. %, at least 3.2 wt. %, at least 3.3 wt. %, at least 3.4 wt. %, at least 3.5 wt. %, at least 3.6 wt. %, at least 3.7 wt. %, at least 3.8 wt. %, at least 3.9 wt. %, at least 4.0 wt. %, at least 4.1 wt. %, at least 4.2 wt. %, at least 4.3 wt. %, at least 4.4 wt. %, at least 4.5 wt. %, at least 4.6 wt. %, at least 4.7 wt. %, at least 4.8 wt. %, at least 4.9 wt. %, at least 5.0 wt. %, and at most 10 wt. %, at most 9.9 wt. %, at most 9.8 wt. %, at most 9.7 wt. %, at most 9.6 wt. %, at most 9.5 wt. %, at most 9.4 wt. %, at most 9.3 wt. %, at most 9.2 wt. %, at most 9.1 wt. %, at most 9.0 wt. %, at most 8.9 wt. %, at most 8.8 wt. %, at most 8.7 wt. %, at most 8.6 wt. %, at most 8.5 wt. %, at most 8.4 wt. %, at most 8.3 wt. %, at most 8.2 wt. %, at most 8.1 wt. %, at most 8.0 wt. %, at most 7.9 wt. %, at most 7.8 wt. %, at most 7.7 wt. %, at most 7.6 wt. %, at most 7.5 wt. %, at most 7.4 wt. %, at most 7.3 wt. %, at most 7.2 wt. %, at most 7.1 wt. %, at most 7.0 wt. %, at most 6.9 wt. %, at most 6.8 wt. %, at most 6.7 wt. %, at most 6.6 wt. %, at most 6.5 wt. %, at most 6.4 wt. %, at most 6.3 wt. %, at most 6.2 wt. %, at most 6.1 wt. %, at most 6.0 wt. %, preferably between 0.5 wt. % and 7.5 wt. %, preferably between 0.84 wt. % and 2.7 wt. %, preferably between 0.84 wt. % and 4.5 wt. %, or between 0.7 wt. % and 5.0 wt. %, or more preferably between 2.1 wt. % and 2.7 wt. %, between 0.84 wt. % and 2.7 wt. %, or more preferably between 3.28 wt. % and 9 wt. %.

In an embodiment, the amount of the soluble fiber in the cream substitute is comprised between 0.5 wt. % and 5.0 wt. %, preferably comprised between 1.0 wt. % and 4 wt. %, preferably at most 2.0 wt. %, at most 3.0 wt. %, at most 4.0 wt. %, at most 5.0 wt. %, and at least 0.5 wt. %, at least 1.0 wt. %, at least 1.5 wt. %, at least 2.0 wt. %, at least 2.5 wt. %, at least 3.0 wt. %, at least 3.5 wt. %, at least 4.0 wt. %.

In an embodiment, the pH of the cream substitute is comprised between 6 and 8, more preferably between 6.5 and 7.5.

In a preferred embodiment, the cream substitute is an ice-cream. The viscosity of the ice cream is comprised between 100 cps and 1000 cps, preferably between 200 cps and 800 cps, more preferably between 300 cps and 600 cps. The viscosity of the ice cream is at least 100 cps, at least 200 cps, at least 300 cps, at least 400 cps, at least 500 cps, at least 600 cps and at most 1000 cps, at most 900 cps, at most 800 cps, at most 700 cps.

The complete melting time of the ice-cream is comprised between 150 minutes and 360 minutes, preferably between 170 and 320 minutes, more preferably between 200 and 300 minutes. The complete melting time of the ice-cream is at least 150 minutes, at least 160 minutes, at least 170 minutes, at least 180 minutes, at least 190 minutes, at least 200 minutes, at least 210 minutes, at least 220 minutes, at least 230 minutes, at least 240 minutes, at least 250 minutes, at least 260 minutes, at least 270 minutes and at most 360 minutes, at most 350 minutes, at most 340 minutes, at most 330 minutes, at most 320 minutes, at most 310 minutes, at most 300 minutes, at most 290 minutes, at most 280 minutes.

The hardness (measured at 15 mm of depth) of the ice cream is comprised between 200 g and 1000 g, preferably between 300 g and 800 g, more preferably between 400 g and 700 g. The hardness (measured at 15 mm of depth) is at least 200 g, at least 250 g, at least 300 g, at least 400 g, at least 450 g, at least 500 g, at least 550 g, at least 600 g, at least 650 g and at most 1000 g, at most 950 g, at most 900 g, at most 850 g, at most 800 g, at most 750 g, at most 700 g.

In a preferred embodiment, the cream substitute is a culinary cream. The viscosity of the culinary cream is comprised between 50 cps and 1000 cps, preferably between 150 cps and 800 cps, more preferably between 300 cps and 600 cps. The viscosity of the culinary cream is at least 50 cps, at least 100 cps, at least 150 cps, at least 200 cps, at least 250 cps, at least 300 cps, at least 350 cps, at least 400 cps, at least 450 cps, at least 500 cps, at least 550 cps and at most 1000 cps, at most 950 cps, at most 900 cps, at most 850 cps, at most 800 cps, at most 750 cps, at most 700 cps, at most 650 cps, at most 600 cps. The stability of the fat phase is at least 75%, preferably at least 85%, more preferably 100%. The sediment is at most 5%, at most 3%, 0%.

In a preferred embodiment, the cream substitute is a milk dessert substitute. In one embodiment, the milk dessert substitute is made without sugar, more preferably in the presence of sweetener.

The hardness of the milk dessert substitute is comprised between 25 and 100 g, preferably between 35 g and 80 g, more preferably between 40 g and 75 g. The hardness of the milk dessert substitute is at least 25 g, at least 30 g, at least 35 g, at least 40 g, at least 45 g, at least 50 g, at least 55 g and at most 100 g, at most 95 g, at most 90 g, at most 85 g, at most 80 g, at most 75 g, at most 70 g, at most 65 g, at most 60 g.

The elasticity of the milk dessert substitute is comprised between 25% and 60%, preferably between 30 and 55%, more preferably between 40% and 50%.

In a preferred embodiment, the cream substitute is a whipped cream. The whipped cream has an overrun comprised between 150% and 250%, preferably between 175% and 225%, more preferably between 185% and 215%. The hardness of the whipped cream is comprised between 25 g and 100 g, preferably between 35 g and 85 g, more preferably between 45 g and 75 g. The whipped cream is at least 25 g, at least 30 g, at least 35 g, at least 40 g, at least 45 g, at least 50 g, at least 55 g and at most 100 g, at most 95 g, at most 90 g, at most 85 g, at most 80 g, at most 75 g, at most 70 g, at most 65 g, at most 60 g. The viscosity of the whipped cream is comprised between 50 cps and 1000 cps, preferably between 150 cps and 800 cps, more preferably between 300 and 600 cps. The viscosity of the whipped cream is at least 50 cps, at least 100 cps, at least 150 cps, at least 200 cps, at least 250 cps, at least 300 cps, at least 350 cps, at least 400 cps, at least 450 cps, at least 500 cps, at least 550 cps and at most 1000 cps, at most 950 cps, at most 900 cps, at most 850 cps, at most 800 cps, at most 750 cps, at most 700 cps, at most 650 cps, at most 600 cps.

The present description in particular further captures the following embodiments or combination of embodiments herein below presented as numbered statements.

1. Cream substitute comprising intact pulse protein in an amount comprised between 0.5 wt. % and 10 wt. % based on the total weight of the cream substitute, more preferably between 0.5 wt. % and 7.5 wt. %, even more preferably between 0.5 wt. % and 5 wt. %.
2. The cream substitute according to statement 1, wherein said pulse protein is the main protein present in the cream substitute and wherein said cream substitute may comprise proteins selected from caseinate, casein, whey, soy, oat, coconut, rice, gluten, nut, wheat and almonds, but in an amount lower than that of the pulse protein and wherein the pulse protein is the main protein present in the cream substitute, other protein being selected from caseinate, casein, whey, soy, oat, coconut, rice, gluten, nut, wheat and almonds.
3. The cream substitute according to statement 1 or 2, wherein said pulse protein has not been subjected to a hydrolysis process.
4. The cream substitute according to any one of statements 1 to 3, wherein said pulse protein possess a degree of hydrolysis of 5% or lower, preferably of 4% or lower, preferably of 3% or lower.
5. Cream substitute according to any one of statements 1 to 4, wherein the cream substitute comprises pulse chosen from lentils, beans, peas and chickpeas and combinations thereof.
6. Cream substitute according to any one of statements 1 to 5, wherein the cream substitute contains a soluble fiber selected from inulin, gluco-oligosaccharides (GOSs), iso-malto-oligosaccharides (IMOs), galacto-oligosaccharides (TOSs), pyrodextrins, polydextrose, branched maltodextrins, indigestible dextrins and soluble oligosaccharides derived from oleaginous plants or protein-producing plants, preferably wherein the soluble fiber is chosen from inulin, FOSs more preferably wherein the preferred source of fiber is from chicory root.
7. Cream substitute according to any one of statements 1 to 6, wherein the cream substitute comprises pulse protein as the sole source of vegetable protein, preferably wherein the pulse protein is the sole source of protein.
8. Cream substitute according to any one of statements 1 to 7, wherein the cream substitute is dairy free, i.e. is substantially free of all dairy-derived ingredients, preferably wherein no dairy-derived ingredients are added to the cream substitute and wherein less than 1 wt. %, such as less than 0.9 wt. %, 0.8 wt %, 0.7 wt. %, 0.6 wt. %, 0.5 wt. %, 0.4 wt. %, 0.3 wt. %, 0.2 wt. %, 0.1 wt. % or less of dairy-derived ingredients are present in the cream substitute.
9. Cream substitute according to any one of statements 1 to 8, wherein the preferred pulse protein is pea protein, more preferably pea protein isolate.
10. Use of the cream substitute according to any one of statements 1 to 9, for producing an ice cream, a whipped cream, a culinary cream, or a milk dessert substitute, preferably wherein the milk dessert substitute is made without lactic ferments.
11. Cream substitute, more specifically ice-cream, comprising intact pulse protein in an amount comprised between 0.5 wt. % to 10 wt. % based on the total weight of the cream substitute, more preferably between 0.6 wt. % and 7.5 wt. %, even more preferably between 0.7 wt. % and 5.0 wt. %, and wherein the pulse protein is the main protein present in the cream substitute, other proteins being selected from caseinate, casein, whey, soy, oat, coconut, rice, gluten, nut, wheat and almonds; and a soluble fiber, preferably in an amount comprised between 0.5 wt. % and 5.0 wt. %. 12. The cream substitute according to any one of statements 1 to 9 and 11, used for making an ice-cream.

13. An ice cream comprising the cream substitute according to any one of statements 1 to 9 and:
    a soluble fiber in an amount comprised between 0.5 wt. % and 5 wt. %
    sugar in an amount of from 0 wt. % to 20 wt. %,
    glucose and/or dextrose and/or fructose in an amount of from 0 wt. % to 20 wt %,
    vegetable fat in an amount of from 1.5 wt. % to 5 wt. %, and optionally
    additives selected from: flavours, colorants, stabilisers, thickeners, gelling agents, emulsifiers, bulking agent in an amount of from 0.05 wt. % to 10 wt. %.

14. The ice cream according to statement 13, having a viscosity comprised between 100 cps and 1000 cps; a complete melting time comprising between 150 minutes and 360 minutes; and/or a hardness (measured at 15 mm of depth) comprising between of 200 g and 1000 g.

15. The cream substitute according to any one of statements 1 to 9, used for making a culinary cream.

16. A culinary cream comprising the cream substitute according to any one of statements 1 to 9 and:
    fructose and/or glucose and/or saccharose in an amount of from 0 wt. % to 4 wt. %,
    vegetable oil in an amount of from 0 wt. % to 20 wt. %, and optionally
    additives selected from: flavours, colorants, stabilisers, thickeners, gelling agents, emulsifiers, bulking agent in an amount of from 0.05 wt. % to 10 wt. %.

17. The culinary cream according to claim 16, having a viscosity comprised between 50 cps and 1000 cps, a fat phase of above of 75%; and/or a sediment phase of less than 5%.

18. The cream substitute according to any one of claims 1 to 9, used for making a milk dessert substitute.

19. A milk dessert substitute comprising the cream substitute according to any one of statements 1 to 9, and further comprising:
    sugar in an amount of from 7 wt. % to 15 wt. %,
    starch in an amount of from 0 wt. % to 5 wt. %,
    vegetable fat in an amount of from 0 wt. % to 5 wt. %, and optionally
    additives selected from: flavours, colorants, stabilisers, thickeners, gelling agents, emulsifiers, sweetener, bulking agent in an amount of from 0.05 wt. % to 5 wt. %.
    20. The milk dessert substitute according to statement 19, having a hardness comprised between 25 g and 100 g; and/or an elasticity of between 25% and 60%.

21. The cream substitute according to any one of statements 1 to 9, used for making a whipped cream.

22. A whipped cream comprising the cream substitute according to any one of statements 1 to 9, and further comprising:
    sugar in an amount of from 0 wt. % to 15 wt. %,
    vegetable oil in an amount of from 15 wt. % to 30 wt. %, and optionally
    additives selected from: flavours, colorants, stabilisers, thickeners, gelling agents, emulsifiers, bulking agent, sweeteners in an amount of from 0.05 wt. % to 2 wt. %.

23. The whipped cream according to statement 22, wherein said whipped cream has an overrun comprised between 150% and 250%; a hardness at best overrun comprised between 25 g and 100 g; and/or a viscosity before being whipped comprised between 50 cps and 1000 cps.

24. Use of pulse protein for replacing milk protein in a cream substitute.

25. Use according to statement 24, wherein substantially all milk protein is replaced by pulse protein.

Examples

Protocols used in the following examples (unless otherwise specified)

Viscosity

Viscosity was measured on a viscometer Brookfield RVT, at speed 50 with a spindle 1, 2 or 3 depending on the viscosity.

The viscosity is measured in a beaker of 500 ml, with a sufficient amount of liquid to immerse the probe. The viscosity is expressed in centipoise, cps.

For the non-dairy frozen dessert, the viscosity is measured after one night melting in the fridge and after homogenisation of the melted product with a spoon.

Stability of the Liquid or the Foam

A centrifuge cylindric tube of 30 ml is filled with 25 ml of the culinary cream and centrifuged 10 minutes at 1800G.

The stability is evaluated either by percentage weight of the sediment or by percentage height of the different phases. The distinct phases, measured with a ruler, are noted in percentages Taste The taste is evaluated by sensory analysis of a trained panel.

pH Measurement

The pH of the cream substitute is measured in a beaker of 30 ml, at room temperature, with a Mettler Toledo InLab Solids Pro-ISM probe using a Knick Portavo apparatus.

Hardness

The hardness is measured with a Texture analyser Lloyd model TA1.

The hardness of the whipped cream was measured with these parameters:
    Probe: grid of 35 mm,
    Compression test with holding time 15 mm (Speed: 3 mm/sec), holding 30 seconds, return to zero (2 mm/sec).
The hardness is the maximum force in g (after 15 mm of compression).
The hardness of the frozen ice cream was measured with these parameters after 1, 2, 5, 10 and 15 sec):
    Compression test with a probe pic of 5 mm,
    Speed of 1 mm/sec
The hardness is the maximum force in g (after 1, 2, 5, 10 and 15 mm of depth).
The hardness of the milk dessert substitute was measured with these parameters:
    Compression test with a probe cylinder of 25 mm,
    Speed of 0.5 mm/sec and
    Stopped after 15 mm.
    A bottle of 40 ml (diameter of 28 mm and height of 70 mm) is used for the measurement.
The hardness is the mean force (in g) between 8 and 30 seconds of holding time.

Colour

The colour is determined with the ChromaMeter MINOLTA CR-5, Petri dish mode. 1 is the theoretical limit for significant differentiation between the reference and the sample. ΔE*ab expresses the colour difference between two objects according to 3 points in the L*a*b* colour space (L: for lightness, a: for the colour range between green and red and b: for the colour range between yellow and blue). The chromameter provides the L, a and b values and by using a specific formula, the ΔE*ab is obtained.

Elasticity

The elasticity was measured with a Texture analyser Lloyd model TA1.

The elasticity of the milk dessert was measured as follows:

Compression test with a probe cone of 45° C.,
Holding time of 30 seconds,
Speed: 1 mm/sec (20 mm) The elasticity is calculated as:
(Max force/Force after holding time)*100 (in %).

Determining Complete Melting Time

Melting Test:

Frozen ice cream (500 ml) is laid on a grid at room temperature. Then the melting ice cream is weighted each 10 minutes until the melting is complete.

Visual evolution of the melting is evaluated. The time for complete melting is noted.

Overrun

Overrun is the ratio between the weight of the cream before whipping and the weight of the cream after whipping for a similar volume, expressed in percent.

The overrun of a whipped cream is measured as follows: A snap cap of 200 ml is tare (P1 also abbreviated W1) and then filled completely with the cream and the weight (P2 also abbreviated W2) is noted. Then 500 ml of cream is put into the bowl of a Kenwood food-processor and whipped until desired texture is achieved (measurement of overrun is after 1, 2, 3, 4, and 5 min of whipping). The snap cap is then filled completely with the whipped cream and the weight (P3 also abbreviated W3) is noted.

Overrun=(100*weight before whipping/weight after whipping)−100 (expressed in %)

Overrun=(100*(W2−W1)/(W3−W1))−100 (expressed in %)

Example 1: Some Examples of Cream Substitutes 1.1. Whipped cream, Product A

The ingredients are listed in Table 1.

Preparation:

The water is weighed in an inox beaker. All dry ingredients are blended and then dispersed in the water with standard helix. Then the oil is added and mixed. The mixture is heated at 60° C. while mixing and then homogenised with ultraturrax for 1 min at speed 4. The mixture is then heated at 90° C. while mixing. Finally, the mixture is cooled down at 20° C. while mixing and stored in the fridge for the night.

TABLE 1

| Ingredients/trials | Product A |
| --- | --- |
| Water | 64.16 |
| Pea protein isolate (A)# | 2.50 |
| Fructose-glucose syrup | 2.30 |
| Sodium hexametaphosphate | 0.20 |
| Spray-dried maltodextrin (18 DE) | 3.00 |
| Salt | 0.08 |
| Potassium dihydrogen phosphate | 0.06 |
| Sucrose ester | 0.10 |
| Lactem* | 0.50 |
| Crystal sugar | 2.00 |

TABLE 1-continued

| Ingredients/trials | Product A |
| --- | --- |
| Hydrogenated palm kernel oil | 25.00 |
| Sodium stearoyl lactylate | 0.10 |
| Total | 100 |

*Rikemal LV-22;
(A)# is Pisane™ C9

Pisane™ C9 contains between 80 and 83%, such as about 81.7% intact pea protein by weight of the isolate (between 82 and 90% on dry matter of the isolate): 2.5 wt. % Pisane™ C9 thus corresponds to from about 2.0 to about 2.1 wt. % pea protein, such as about 2.05 wt. % pea protein.

Results

The results are presented in Table 2. The product A was compared to a commercial product made of soy without milk.

TABLE 2

| Properties | Commercial product | Product A |
| --- | --- | --- |
| Overrun (%) | 295 | 196 |
| Hardness at best overrun (cps) | 63.5 | 77.2 |
| Viscosity of liquid solution (cps) | 224 | 360 |

1.2. Culinary Cream, Product B

The ingredients are presented in Table 3.

Preparation:

All dry ingredients are blended and then dispersed in water. The oil is added while mixing. The pH was adjusted at 7.0 with a citric acid solution. The mixture is sterilized on a heat plate exchanger and homogenized at 50/150 bars at 70-75° C. Sterilization is performed at 140° C. for 5 seconds. Finally, the mixture is cooled at 20-25° C. and filled in bottles in aseptic conditions.

TABLE 3

| Ingredients | Product B |
| --- | --- |
| Water | 77.71 |
| Sunflower oil | 16.50 |
| Pea protein isolate (A)* | 2.50 |
| Fructose-glucose syrup | 2.30 |
| Thickener (E412-E415) | 0.28 |
| Monoglyceride | 0.20 |
| Sodium hexametaphosphate | 0.20 |
| Gellan gum | 0.10 |
| Sucrose ester | 0.10 |
| Carrageenan | 0.05 |
| Salt | 0.05 |
| Citric acid anhydrous | 0.01 |
| Total | 100.00 |

*(A) is Pisane™ C9

Pisane™ C9 contains between 80 and 83%, such as about 81.7% intact pea protein by weight of the isolate (between 82 and 90% on dry matter of the isolate): 2.5 wt. % Pisane™ C9 thus corresponds to from about 2.0 to about 2.1 wt. % pea protein, such as about 2.05 wt. % pea protein.

Results

TABLE 4

| Properties | Product B |
|---|---|
| Visual aspect | 100% stable |
| Viscosity | 86 cps |
| pH | 6.82 |
| Taste | Slightly sweet, low vegetable taste, better than a cream substitute comprising soy protein |

1.3. Frozen Dessert, Product C

The ingredients are listed in Table 5.

Preparation:

All dry ingredients are mixed together and then are added to water at 45-50° C. with the glucose syrup and the melted fat. The mixture is homogenized at 60° C., at 180 bars. The mixture is then pasteurized on heat plate exchanger at 85° C. for 30 seconds. Then the preparation is cooled down at 5° C. while mixing for 18 hours. Finally, the mixture is frozen in a continuous freezer and filled for storing at −20° C.

TABLE 5

| Ingredients | Product C |
|---|---|
| Water | 64.80 |
| Crystal sugar | 9.00 |
| Glucose syrup 38 DE | 6.00 |
| Spray-dried maltodextrin | 6.00 |
| Dextrose | 4.00 |
| Inulin | 3.00 |
| Vegetable fat (coprah) | 2.60 |
| Vanilla extract | 2.50 |
| Pea protein isolate (A)* | 1.58 |
| Emulsifier & stabiliser system (Cremodan ® SE30) | 0.50 |
| Colouring E110 (liquid) | 0.02 |
| Total | 100 |

*(A) is Pisane ™ C9

Pisane™ C9 contains between 80 and 83%, such as about 81.7% intact pea protein by weight of the isolate (between 82 and 90% on dry matter of the isolate): 1.58 wt. % Pisane™ C9 thus corresponds to from about 1.26 to about 1.31 wt. % pea protein, such as about 1.29 wt. % pea protein.

Results

The results are presented in Table 6.

TABLE 6

| Properties | Product C |
|---|---|
| Viscosity (cps) | 240 |
| Hardness 1 mm | 79.7 |
| Hardness 2 mm | 111.3 |
| Hardness 5 mm | 201.5 |
| Hardness 10 mm | 325.3 |
| Hardness 15 mm | 440.8 |

With this product, the viscosity was measured before overrun and freezing. The ice cream was melted after 180 minutes and the melting (i.e. the melted product) was complete, liquid, and homogenous.

1.4. Dessert Cream, Product D

All ingredients are listed in Table 7.

Preparation:

Pea protein isolate is dispersed in water with anti-lump helix. The oil is added while mixing and then the mixture is homogenized with Ultraturax for 2 minutes at speed 4. The de-aeration of the mixture is made with a Stephan (vacuum the solution at 3000 rpm). Then the sodium hexametaphosphate is added and the pH of the mixture is adjusted to 6.70 with citric acid solution. All remaining dry ingredients are blended and dispersed in the mixture while mixing at 750 rm. Then the mixture is heated at 80° C. and kept at 80° C. for 10 minutes while mixing. Finally, the mixture is cooled down to 25° C. while mixing and filled into pots for storing at 4° C.

TABLE 7

| Ingredients | Product D |
|---|---|
| Water | 78.04 |
| Crystal cane sugar | 13.00 |
| Pea protein isolate (A)* | 3.90 |
| Modified starch | 2.50 |
| Sunflower oil | 1.60 |
| Tricalcium phosphate anhydrous | 0.29 |
| Caramel colouring | 0.25 |
| Sodium hexametaphosphate | 0.15 |
| Caramel flavour | 0.10 |
| Instant coffee | 0.05 |
| Carrageenan | 0.05 |
| Citric acid anhydrous | 0.066 |
| TOTAL | 100 |

*(A) is Pisane ™ C9

Pisane™ C9 contains between 80 and 83%, such as about 81.7% intact pea protein by weight of the isolate (between 82 and 90% on dry matter of the isolate): 3.90 wt. % Pisane™ C9 thus corresponds to from about 3.12 to about 3.24 wt. % pea protein, such as about 3.18 wt. % pea protein.

Results

The results are presented in Table 8. The product D was compared to a commercial product made of soy without milk.

TABLE 8

| Properties | Commercial product | Product D |
|---|---|---|
| Hardness | 38.76 g | 67.86 g |
| Elasticity | 30.50% | 37.35% |
| Stability | 100% | 100% |

1.5. Yogurt, Product E

All ingredients are listed in Table 9.

Preparation:

The process is divided in 3 parts:

Part 1: The pea protein isolate and the calcium are dispersed in water. Then fat is added, and the pH is adjusted to 7.0 with lactic acid. The mixture is homogenized at 50/150 bars, at 70-75° C. and heated at 90° C. for seconds. Finally, the mixture is cool down and store at 4° C. if necessary.

Part 2: The rest of the ingredients (sugar, pectin, salt) are dispersed and heated to 60° C. Then the mixture is homogenized and heat to 90° C. for seconds. Finally, the mixture is cooled down to 45° C.

Part 3: The culture (re-activated) is added to the solution, and incubated at 45° C. until pH 4,6 is reach. Then the yogurt is cooled down and the flavour and the fruit preparation are added, and the mixture is homogenized. The pots are filled and store at 4° C.

TABLE 9

| Ingredients | Product E |
| --- | --- |
| Water | 69.98 |
| Pea protein isolate (A)* | 4.12 |
| Crystal sugar | 5.95 |
| Sunflower oil | 1.70 |
| Inulin | 2.30 |
| Dicalcium phosphate anhydrous | 0.32 |
| Salt | 0.05 |
| Native maize starch | 0.26 |
| Pectin | 0.17 |
| L(+) Lactic acid | 0.03 |
| Cultures | 0.03 |
| Yogurt flavour | 0.09 |
| Pineapple flavour | 0.01 |
| Pineapple fruit filling | 15.00 |
| TOTAL | 100 |

*(A) is Pisane ™ C9

Pisane™ C9 contains between 80 and 83%, such as about 81.7% intact pea protein by weight of the isolate (between 82 and 90% on dry matter of the isolate): 4.12 wt. % Pisane™ C9 thus corresponds to from about 3.30 to about 3.42 wt. % pea protein, such as about 3.37 wt. % pea protein.

Results:
The hardness of the yogurt is 55.30 g.

Example 2: Non-Dairy Whipping Cream 2.1. Reference Cream with 2.5% Pea Protein Isolate
All ingredients are listed in Table 10.

Preparation:
The fat is melted at 50° C. and a blend is made with all dry ingredients. Water is heated to 50° C. and the blend is dispersed in water (1200 rpm), heated to 90° C. (800 rpm) and cooled down to 80° C. Homogenization is at 150 bars (50/100), followed by cooling down to 10° C.

TABLE 10

| Ingredients | In g |
| --- | --- |
| Water | 63.77 |
| Hydrogenated palm kernel oil | 25.00 |
| Spray-dried maltodextrin (18 DE) | 3.00 |
| Pea protein isolate (A)* | 2.50 |
| Fructose-glucose syrup | 2.30 |
| Crystal sugar | 2.00 |
| Lactem | 0.75 |
| Sucrose ester (E473) | 0.40 |
| Sodium hexametaphosphate (E452) | 0.20 |
| Salt | 0.08 |
| TOTAL | 100 |

*(A) is Pisane ™ C9

Pisane™ C9 contains between 80 and 83%, such as about 81.7% intact pea protein by weight of the isolate (between 82 and 90% on dry matter of the isolate): 2.5 wt. % Pisane™ C9 thus corresponds to from about 2.0 to about 2.1 wt. % pea protein, such as about 2.05 wt. % pea protein.

Protocols:
Protocols are as described earlier.

2.2. Liquid Cream with Pea Protein Pisane™ C9 at Different Concentrations
All ingredients are listed in Table 11 (in g).

TABLE 11

| Ingredients | Comment | P0 | P1 | P2 | Ref* | P3 | P4 | P5 |
| --- | --- | --- | --- | --- | --- | --- | --- | --- |
| Water | | 66.27 | 65.27 | 64.27 | 63.77 | 63.27 | 62.27 | 61.27 |
| Pea protein isolate | Pisane ™ C9-Cosucra | 0.00 | 1.00 | 2.00 | 2.50 | 3.00 | 4.00 | 5.00 |
| Crystal sugar | | 2.00 | 2.00 | 2.00 | 2.00 | 2.00 | 2.00 | 2.00 |
| Fructose-glucose syrup | Fructomix F50/71%-Belgosuc | 2.30 | 2.30 | 2.30 | 2.30 | 2.30 | 2.30 | 2.30 |
| Sodium hexametaphosphate | SHMP FG MC-Prayon | 0.02 | 0.02 | 0.02 | 0.02 | 0.02 | 0.02 | 0.02 |
| Spray-dried maltodextrin (18 DE) | C*Dry MD 01915 | 3.00 | 3.00 | 3.00 | 3.00 | 3.00 | 3.00 | 3.00 |
| Salt | | 0.08 | 0.08 | 0.08 | 0.08 | 0.08 | 0.08 | 0.08 |
| Sucrose ester | Sisterna SP70-Siterna | 0.40 | 0.40 | 0.40 | 0.40 | 0.40 | 0.40 | 0.40 |
| Lectern | Rikemal LV-22-Riken Vitamin | 0.75 | 0.75 | 0.75 | 0.75 | 0.75 | 0.75 | 0.75 |
| Hydrogenated palm kernel oil | Ertilor PK 30-Fuji Oil Europe | 25.00 | 25.00 | 25.00 | 25.00 | 25.00 | 25.00 | 25.00 |
| TOTAL | | 100 | 100 | 100 | 100 | 100 | 100 | 100 |

*As a reference, a liquid cream comprising 2.5 wt. % Pisane ™ C9 protein isolate is used. Said pea protein isolate contains between 80 and 83%, such. as about 81.7% intact pea protein by weight of the isolate (between 82 and 90% on dry matter of the isolate). As an example, 1 wt. % Pisane™ C9 thus corresponds to from about 0.80 to about 0.83 wt. % pea protein, such as 0.817 wt. % pea protein.

2.2.1. Results.
Analysis of the Liquid Cream
General Properties

TABLE 12

| | P0*** | P1 | P2 | Ref# | P3 | P4 | P5 |
| --- | --- | --- | --- | --- | --- | --- | --- |
| Visual aspect | More white, thicker, grainy, Not enough emulsified. | Layer (harder) on top, grainy. Not enough emulsified. | Homogenous, a little bit grainy. Limit emulsified. | Homogenous | Homogenous | Homogenous | HomoGenous |

TABLE 12-continued

|     | P0*** | P1   | P2   | Ref# | P3   | P4   | P5   |
| --- | ----- | ---- | ---- | ---- | ---- | ---- | ---- |
| pH  | 6.75  | 7.03 | 7.15 | 7.16 | 7.21 | 7.25 | 7.25 |
| ΔE*ab | —   | 1.99 | 4.25 | 3.77 | 4.68 | 5.55 | 6.17 |

***P0 (0% Pisane ™ C9) has been used as reference;
Ref# is also used as a reference product comprising 2.5 wt. % Pisane C9.

Viscosity

The viscosity of the liquid cream containing 1%, 2%, 2.5%, 3%, 4% and 5% or without Pisane™ C9 is represented in FIG. 1.

Stability

Figure 2:
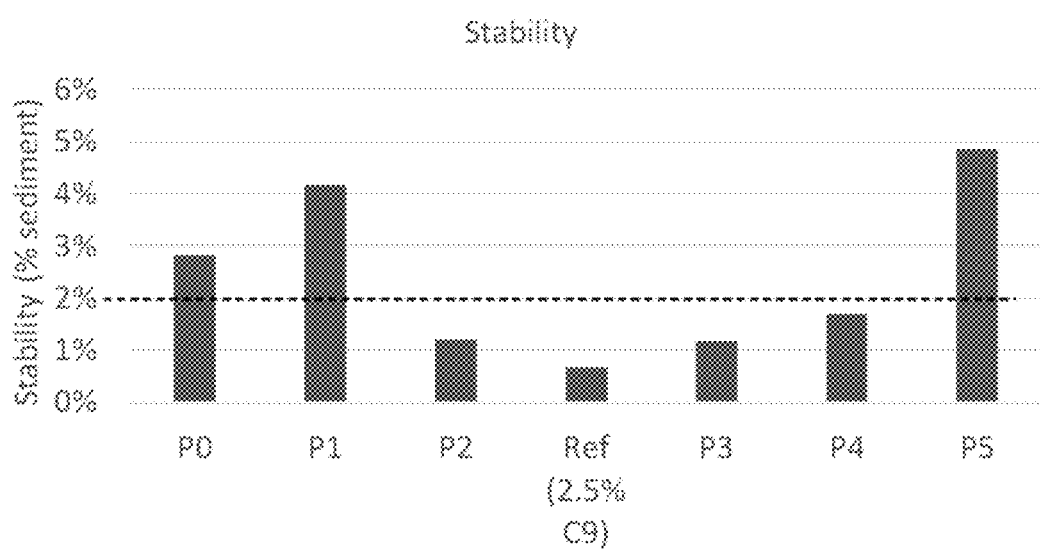
FIG. 2 represents the stability of the liquid cream containing 1%, 2%, 2.5%, 3%, 4% and 5% Pisane™ C9 or without Pisane™ C9 (P0). The dashed horizontal line is a limit of acceptability for stability. Pisane™ C9 at concentration between 2% and 4% improves the stability of the cream.

The stability of the liquid cream containing 1%, 2%, 2.5%, 3%, 4% and 5% or without Pisane™ C9 is represented in FIG. 2. The dashed line is a limit of acceptability for stability. Pisane™ C9 at concentration between 2% and 4% improves the stability of the cream.

Figure 3:
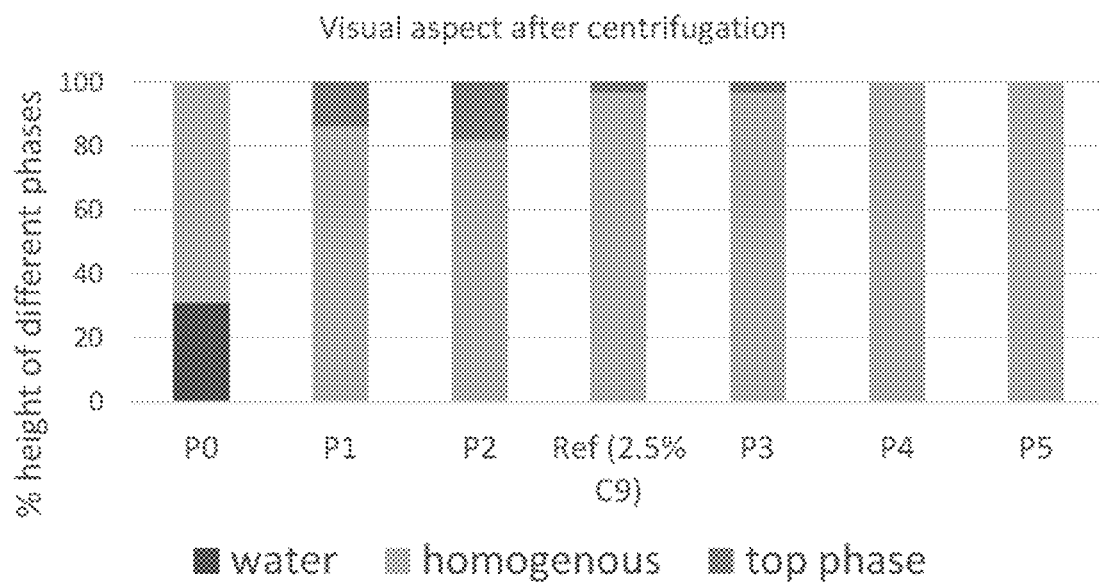
FIG. 3 represents the visual aspect of the liquid cream after centrifugation. Without protein (P0), there is water released after centrifugation of the liquid cream. When Pisane™ C9 is added there is no more water released but a small top phase is released. The stability increases with the concentration of Pisane™ C9.

The visual aspect after centrifugation is represented in FIG. 3. Without protein there is water released after centrifugation of the liquid cream. When Pisane™ C9 is added there is no more water released but a small top phase is released. The stability increases with the concentration of Pisane™ C9.

Analysis of the Whipped Cream

Overrun

Figure 4:
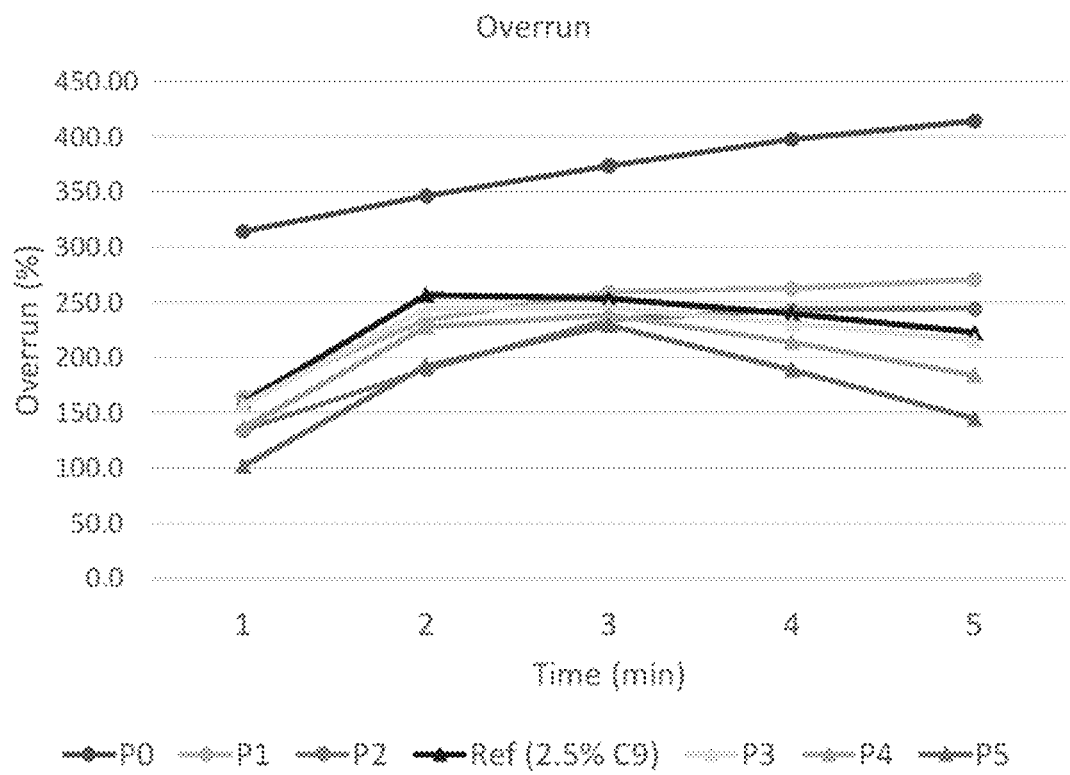
FIG. 4 represents the overrun of the whipped liquid cream containing 1%, 2%, 2.5%, 3%, 4% and 5% Pisane™ C9 or without Pisane™ C9 (P0). The trial without Pisane™ C9 has the best overrun (more than 400%). With Pisane™ C9, the maximum overrun is between 270% and 229%. The maximal overrun decreases slightly with the concentration of protein. Maximal overrun is reached after 5 minutes for trial with 1 to 2% of Pisane™ C9 while the maximum is already reached after 2 minutes for higher concentration.

The overrun of the whipped liquid cream containing 1%, 2%, 2.5%, 3%, 4% and 5% or without Pisane™ C9 is represented in FIG. 4. The trial without Pisane™ C9 has the best overrun (more than 400%). With Pisane™ C9, the maximum overrun is between 270% and 229%. The maximal overrun decreases slightly with the concentration of protein. Maximal overrun is reached after 5 minutes for trial with 1 to 2% of Pisane™ C9 while the maximum is already reached after 2 minutes for higher concentration.

Hardness of the Foam

Figure 5:
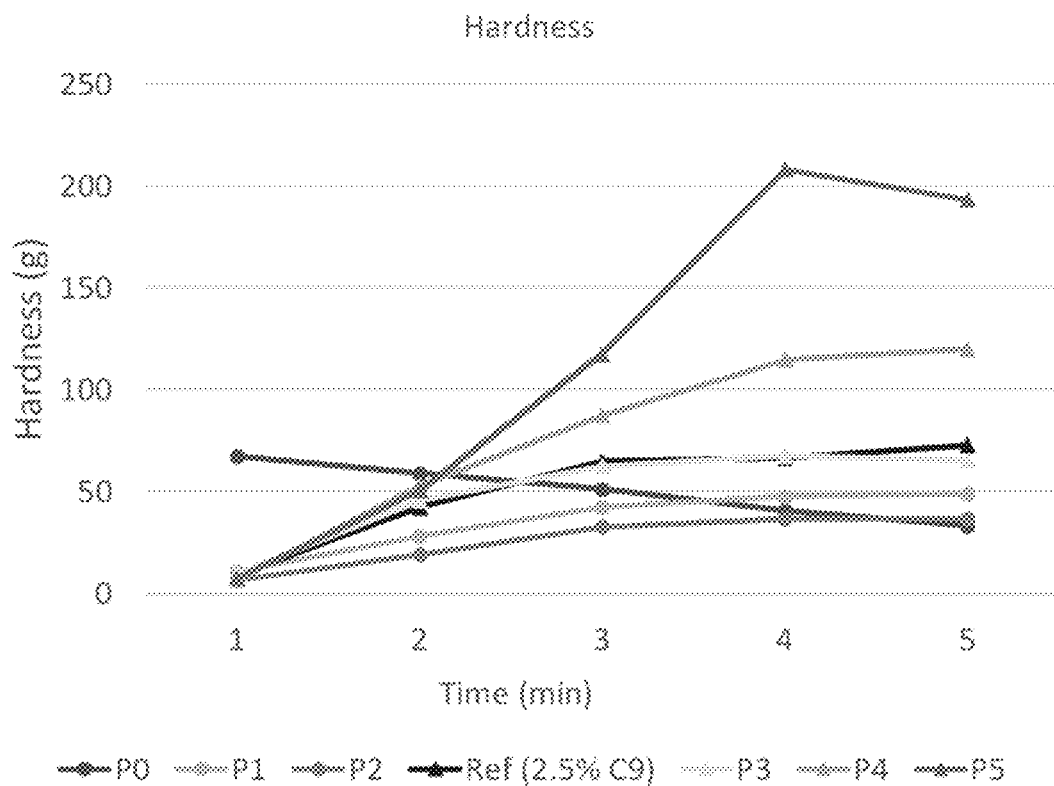
FIG. 5 represents the hardness of the foam of the whipped cream containing 1%, 2%, 2.5%, 3%, 4% and 5% Pisane™ C9 or without Pisane™ C9 (P0).

The hardness of the foam of the whipped cream containing 1%, 2%, 2.5%, 3%, 4% and 5% or without Pisane™ C9 is represented in FIG. 5.

Taste

TABLE 13

| P0 | P1 | P2 | Ref# | P3 | P4 | P5 |
| --- | --- | --- | --- | --- | --- | --- |
| Foam without texture, grainy in mouth | Close to P0, foam a little bit more textured | Still not textured, grainy in mouth. | Acceptable texture, light vegetal taste | More texture than ref but also more vegetal and slightly astringent | Thicker foam, dense, more vegetal and astringent | Very dense Foam, fatty (like butter), vegetal, astringent |

The products with 2.5 wt. % and 3 wt. % of Pisane™ C9 have an acceptable texture of foam and a moderate vegetal taste. Ref # is used as a reference product comprising 2.5 wt. % Pisane C9.

Conclusion

The optimal concentration of Pisane™ C9 is between 2.5 wt. % and 3 wt. % (i.e. corresponding with between 2.1 wt. % and 2.7 wt. % intact pea protein). The presence of Pisane™ C9 is advantageous for:

a good emulsification of the liquid cream
a good texture of the whipped cream (dense and smooth)
a good stability of the liquid cream 2.3. Comparison Between Pulse Protein from Different Origin All ingredients are listed in Table 14 (in g).

TABLE 14

| Ingredients | Ref P2.5 | N 1 | N 2.5 | N 5 | F 1 | F 2.5 | F5 |
| --- | --- | --- | --- | --- | --- | --- | --- |
| Water | 63.77 | 66.27 | 65.27 | 64.27 | 63.27 | 62.27 | 61.27 |
| Pea protein isolate (A)* | 2.50 | 0.00 | 0.00 | 0.00 | 0.00 | 0.00 | 0.00 |
| Pea protein isolate (B)** | 0.00 | 1.00 | 2.50 | 5.00 | 0.00 | 0.00 | 0.00 |
| Faba bean protein isolate (C)*** | 0.00 | 0.00 | 0.00 | 0.00 | 1.00 | 2.50 | 5.00 |
| Crystal sugar | 2.00 | 2.00 | 2.00 | 2.00 | 2.00 | 2.00 | 2.00 |
| Fructose-glucose syrup | 2.30 | 2.30 | 2.30 | 2.30 | 2.30 | 2.30 | 2.30 |
| Sodium hexametaphosphate | 0.02 | 0.02 | 0.02 | 0.02 | 0.02 | 0.02 | 0.02 |
| Spray-dried maltodextrin (18 DE) | 3.00 | 3.00 | 3.00 | 3.00 | 3.00 | 3.00 | 3.00 |
| Salt | 0.08 | 0.08 | 0.08 | 0.08 | 0.08 | 0.08 | 0.08 |
| Sucrose ester | 0.40 | 0.40 | 0.40 | 0.40 | 0.40 | 0.40 | 0.40 |

TABLE 14-continued

| Ingredients | Ref P2.5 | N 1 | N 2.5 | N 5 | F 1 | F 2.5 | F5 |
|---|---|---|---|---|---|---|---|
| Lactem | 0.75 | 0.75 | 0.75 | 0.75 | 0.75 | 0.75 | 0.75 |
| Hydrogenated palm kernel oil | 25.00 | 25.00 | 25.00 | 25.00 | 25.00 | 25.00 | 25.00 |
| TOTAL | 100 | 100 | 100 | 100 | 100 | 100 | 100 |

*(A): Pisane ™ C9-Cosucra;
**(B): Nutralys ® S85F-Roquette;
***(C): Faba bean protein isolate FBCP-90C-1709211 from Fenchem.
Ref P2.5 represents the reference product comprising 2.5 wt. % Pisane C9;
N1 represents the corresponding product comprising Nutralys ® at 1 wt. %, N2.5 represents the corresponding product with 2.5 wt. % Nutralys ®;
N5 represents the corresponding product with 5 wt. % Nutralys ®;
F1 represents the corresponding product with 1 wt. % Faba protein isolate;
F2.5 represents the corresponding product with 2.5 wt. % Faba protein isolate;
F5 represents the corresponding product with 5 wt.% Faba protein isolate.

The protein content (on dry basis) for each Pulse protein used is mentioned below:

TABLE 15

| | Protein on dry basis |
|---|---|
| Nutralys ® S85F | Min 84% |
| Faba bean protein - Fenchem | ≥84% |
| Pisane ™ C9 | 86% ± 2% |

2.3.1. Results
Analysis of the Liquid Cream
General Properties

TABLE 16

| | Ref P 2.5*** | N 1 | N 2.5 | N 5 | F 1 | F 2.5 | F5 |
|---|---|---|---|---|---|---|---|
| Visual aspect | Homogenous | Different layers | Homogenous | Homogenous, thicker | Homogenous | Homogenous | Homogenous, very thick |
| pH | 7.16 | 7.06 | 7.17 | 7.31 | 7.02 | 6.77 | 6.54 |
| ΔE*ab | — | 1.73 | 0.30 | 3.51 | 3.33 | 1.57 | 2.65 |

***P2.5 (2.5% Pisane ™ C9) has been used as reference;
N1 represents the corresponding product comprising Nutralys ® at 1 wt. %, N2.5 represents the corresponding product with 2.5 wt. % Nutralys ®;
N5 represents the corresponding product with 5 wt. % Nutralys ®;
F1 represents the corresponding product with 1 wt. % Faba protein isolate;
F2.5 represents the corresponding product with 2.5 wt. % Faba protein isolate;
F5 represents the corresponding product with 5 wt. % Faba protein isolate.

Viscosity

Figure 6:
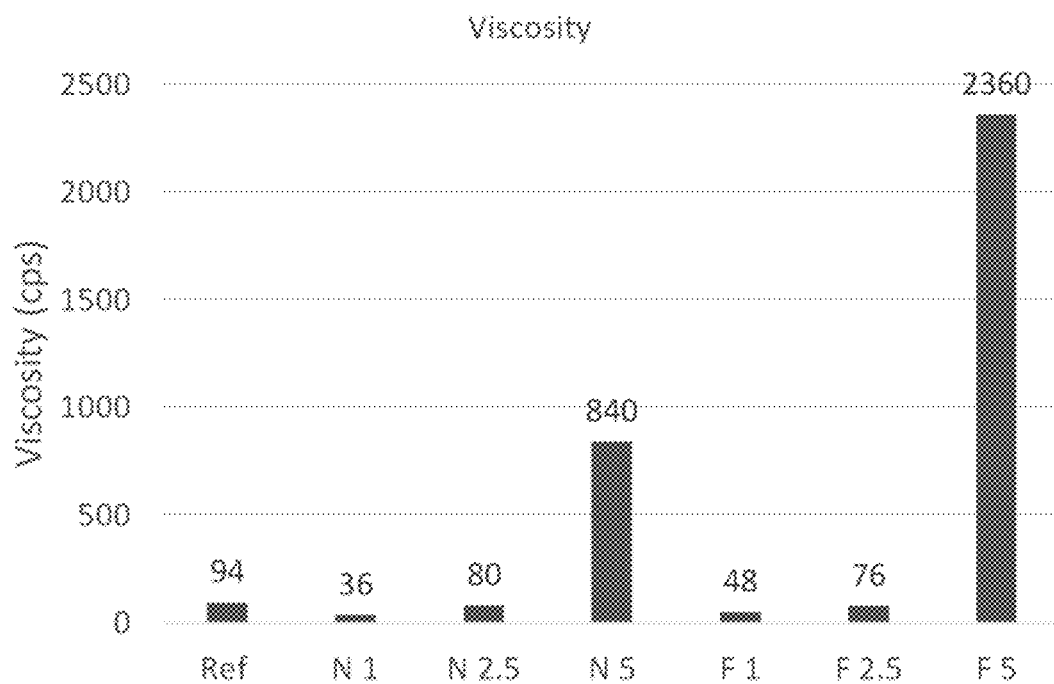
FIG. 6 illustrates the viscosity of liquid cream containing 2.5% Pisane™ C9 (Ref); 1%, 2.5% and 5% Nutralys® S85F (N 1, N 2.5 and N 5); and containing 1%, 2.5% and 5% Faba bean protein (F 1, F 2.5 and F 5). The viscosity of liquid cream is acceptable for 1% and 2.5% of Nutralys® S85F (N1 and N2.5) or Faba bean protein (F1 and F2.5). The values reached are close to the viscosity of cream with Pisane™ C9 at the same concentration. At 5%, the viscosity is strongly increased for Nutralys® S85F (N5) and Faba bean protein (F5).

The viscosity of the liquid cream containing 2.5% Pisane™ C9; 1%, 2.5% and 5% Nutralys® S85F; and containing 1%, 2.5% and 5% *Faba* bean protein is represented in FIG. 6. The viscosity of liquid cream is acceptable for 1% and 2.5% of Nutralys® S85F or *Faba* bean protein. The values reached are close to viscosity of cream with Pisane™ C9 at same concentration. At 5%, the viscosity is strongly increased for Nutralys® S85F and *Faba* bean protein.

Stability

Figure 7:
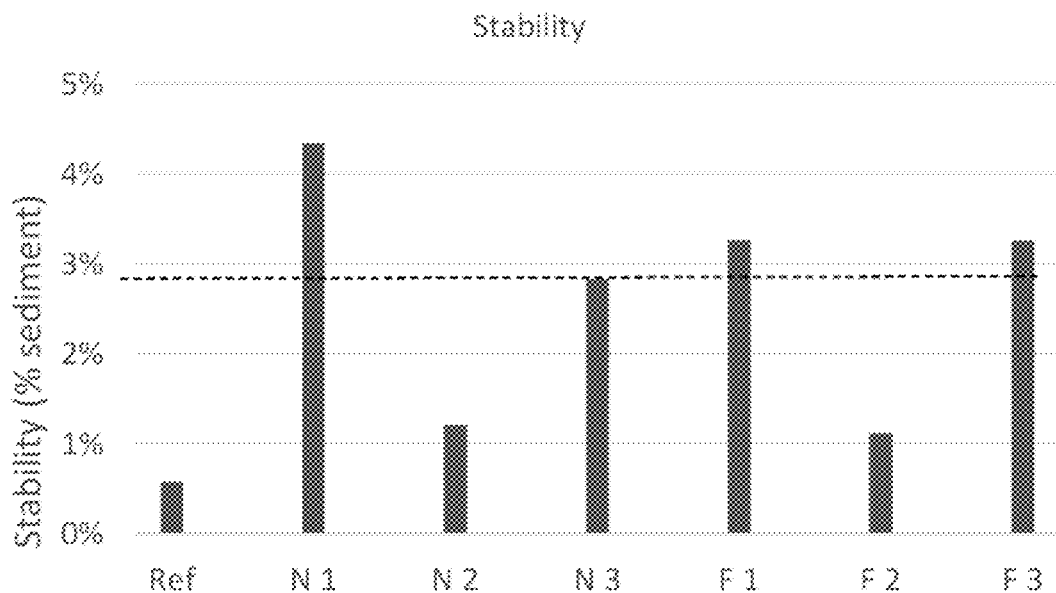
FIG. 7 represents the stability of the liquid cream containing 2.5% Pisane™ C9 (Ref); 1%, 2.5% and 5% Nutralys® S85F (N1, N2 and N3); and 1%, 2.5% and 5% Faba bean protein (F1, F2 and F3). The horizontal dashed line is a limit of acceptability for stability.

The stability of the liquid cream containing 2.5% Pisane™ C9; 1%, 2.5% and 5% Nutralys® S85F; and containing 1%, 2.5% and 5% *Faba* bean protein is represented in FIG. 7. The dashed line is a limit of acceptability for stability.

Figure 8:
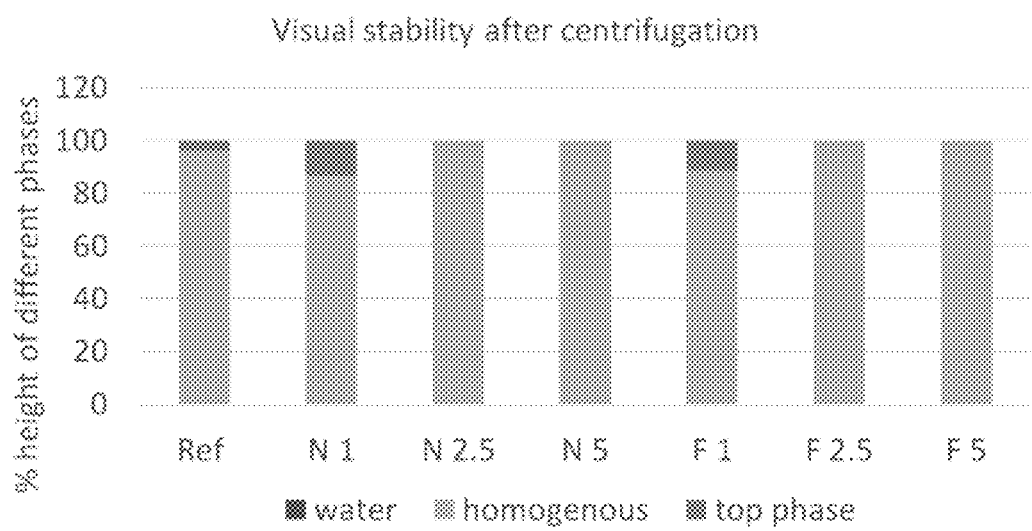
FIG. 8 represents the visual aspect of the cream after centrifugation (2.5% Pisane™ C9 (Ref); 1%, 2.5% and 5% Nutralys® S85F (N 1, N 2.5 and N 5); and 1%, 2.5% and 5% Faba bean protein (F 1, F 2.5 and F 5)).

The visual aspect after centrifugation is represented in FIG. 8.

Analysis of the Whipped Cream

Overrun

Figure 9:
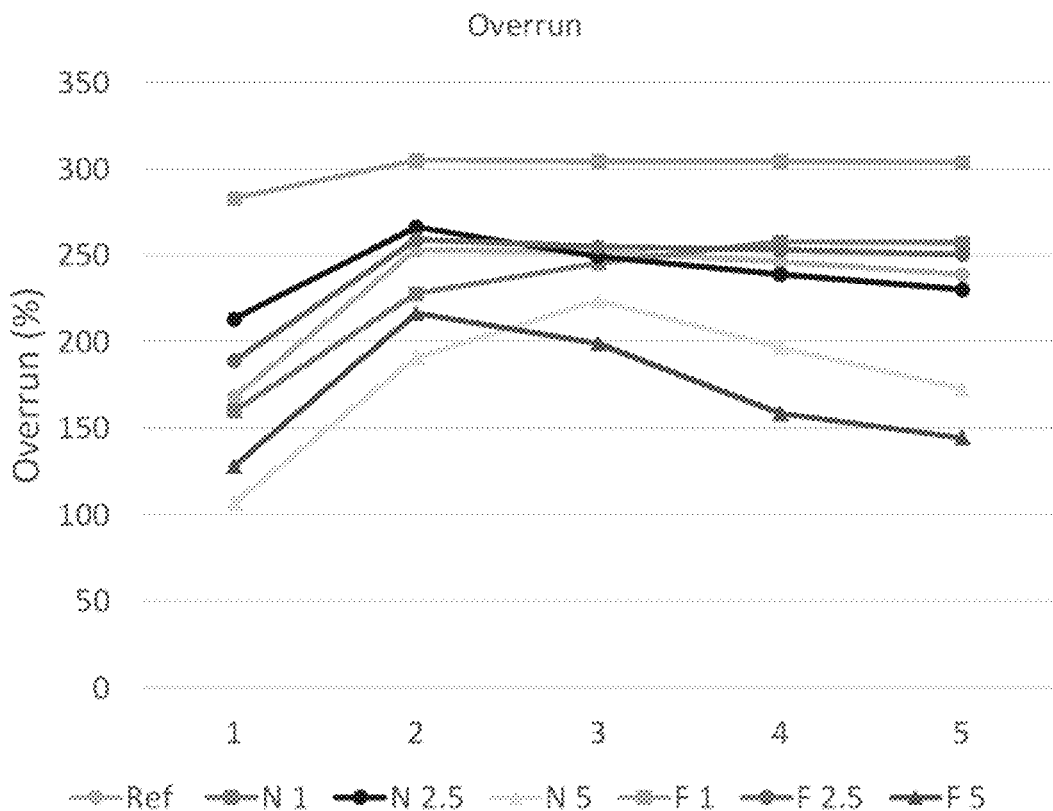
FIG. 9 represents the overrun of the whipped cream containing 2.5% Pisane™ C9 (Ref); 1%, 2.5% and 5% Nutralys® S85F (N 1, N 2.5 and N 5); and 1%, 2.5% and 5% Faba bean protein (F 1, F 2.5 and F 5).

The overrun of the whipped cream containing 2.5% Pisane™ C9; 1%, 2.5% and 5% Nutralys® S85F; and containing 1%, 2.5% and 5% *Faba* bean protein is represented in FIG. 9.

Hardness of the Foam

Figure 10:
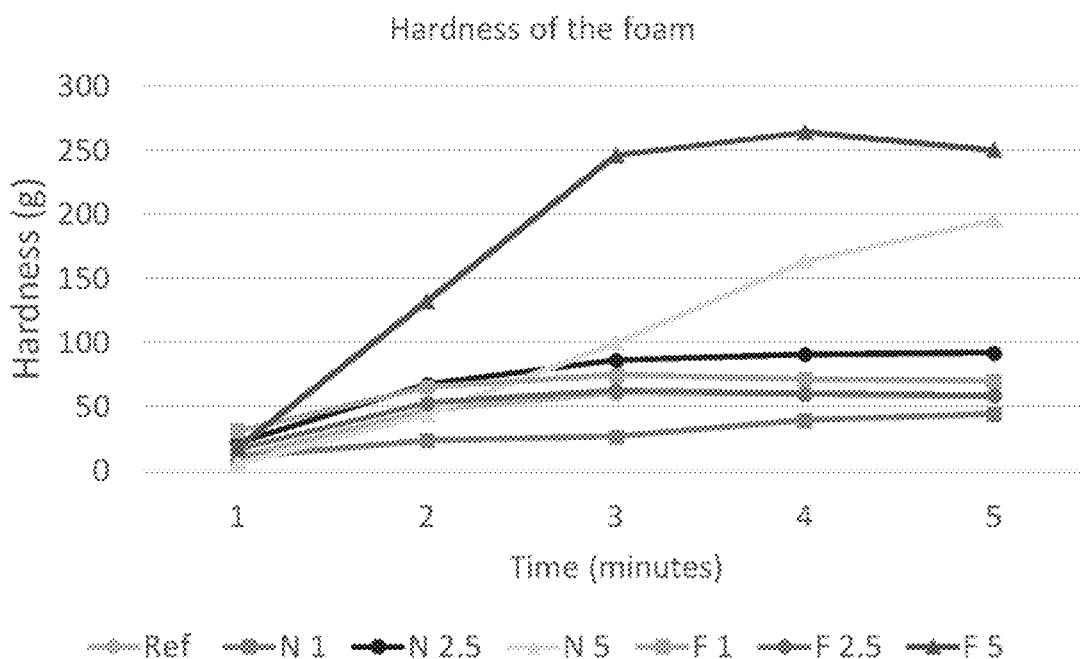
FIG. 10 represents the hardness of the foam of the whipped cream containing 2.5% Pisane™ C9 (Ref); 1%, 2.5% and 5% Nutralys® S85F (N 1, N 2.5 and N 5); and 1%, 2.5% and 5% Faba bean protein (F 1, F 2.5 and F 5).

The hardness of the foam of the whipped cream containing 2.5% Pisane™ C9; 1%, 2.5% and 5% Nutralys® S85F; and containing 1%, 2.5% and 5% *Faba* bean protein is represented in FIG. 10.

Taste

TABLE 17

| Ref P 2.5 | N 1 | N 2.5 | N 5 | F 1 | F 2.5 | F5 |
|---|---|---|---|---|---|---|
| Good texture, light vegetal taste | Sandy, texture very foamy, no enough mouthfeel | Good texture, vegetal taste, less bitter than ref | Foam too textured (fatty) | No sandiness, vegetal after-taste | Slightly sandy, strange taste (egg) | Foam too textured (fatty) and very vegetal |

Ref P 2.5 represents the reference product comprising 2.5 wt. % Pisane 09;
N1 represents the corresponding product comprising Nutralys ® at 1 wt. %, N2.5 represents the corresponding product with 2.5 wt.% Nutralys ®;
N5 represents the corresponding product with 5 wt. % Nutralys ®;
F1 represents the corresponding product with 1 wt. % Faba protein isolate;
F2.5 represents the corresponding product with 2.5 wt. % Faba protein isolate;
F5 represents the corresponding product with 5 wt. % Faba protein isolate.

2.3.2. Conclusion

Pisane™ C9, Nutralys® S85F and *Faba* bean protein can be used in this application. The recommended dosage is the same for all proteins, ie around 2.5 wt. % (for Pisane™ C9 corresponding with between about 2.1 wt % and 2.25 wt. % intact pea protein; for Nutralys®S85F corresponding with minimal 2.1 wt % pea protein; for *Faba* bean protein isolate corresponding with 2.1 wt. % pea protein). At that concentration, overrun profiles and optimal stability is the same for all proteins. Also for taste and texture, a concentration around 2.5 wt. % is the best compromise for all proteins between density of the foam, vegetal taste and texture.

2.4. Addition of Inulin (Soluble Fibre) and Thereby Replacing Maltodextrin as Another Source of Dry Matter In this experiment, maltodextrin (which is not a soluble fiber but a digestible carbohydrate) is replaced with inulin (a vegetable fiber, such as Fibrulin® Instant) in order to keep a similar % of dry matter. The replacement of maltodextrin with inulin vegetable fibers does not materially change the product, and hence is an interesting alternative for health reasons.

All ingredients are listed in Table 18 (in g).

TABLE 18

| Ingredients | Ref P2.5 | +Inulin |
|---|---|---|
| Water | 63.77 | 66.27 |
| Pea protein isolate (A)* | 2.50 | 2.50 |
| Crystal sugar | 2.00 | 2.00 |
| Fructose-glucose syrup | 2.30 | 2.30 |
| Sodium hexametaphosphate | 0.20 | 0.20 |
| Spray-dried maltodextrin (18 DE) | 3.00 | 0.00 |
| Fibruline ®Instant | 0.00 | 3.00 |
| Salt | 0.08 | 0.08 |
| Sucrose ester | 0.40 | 0.40 |
| Lactem | 0.75 | 0.75 |
| Hydrogenated palm kernel oil | 25.00 | 25.00 |
| TOTAL | 100 | 100 |

*(A)Pisane ™C9.
Ref P 2.5 represents the reference product comprising 2.5 wt. % Pisane C9.

2.4.1. Results

Analysis of the Liquid Cream
General Properties

TABLE 19

| | Ref P2.5 | +Inulin |
|---|---|---|
| Visual aspect | Stable | Stable |
| pH | 7.16 | 7.2 |
| Viscosity (cps) | 118 | 66 |

TABLE 19-continued

| | Ref P2.5 | +Inulin |
|---|---|---|
| Stability (% sediment) | 0.67 | 1.20 |
| ΔE*ab | — | 0.52 |

Ref P2.5: Pisane ™C9 at 2.5% (with maltodextrin) has been used as reference.

Figure 11:
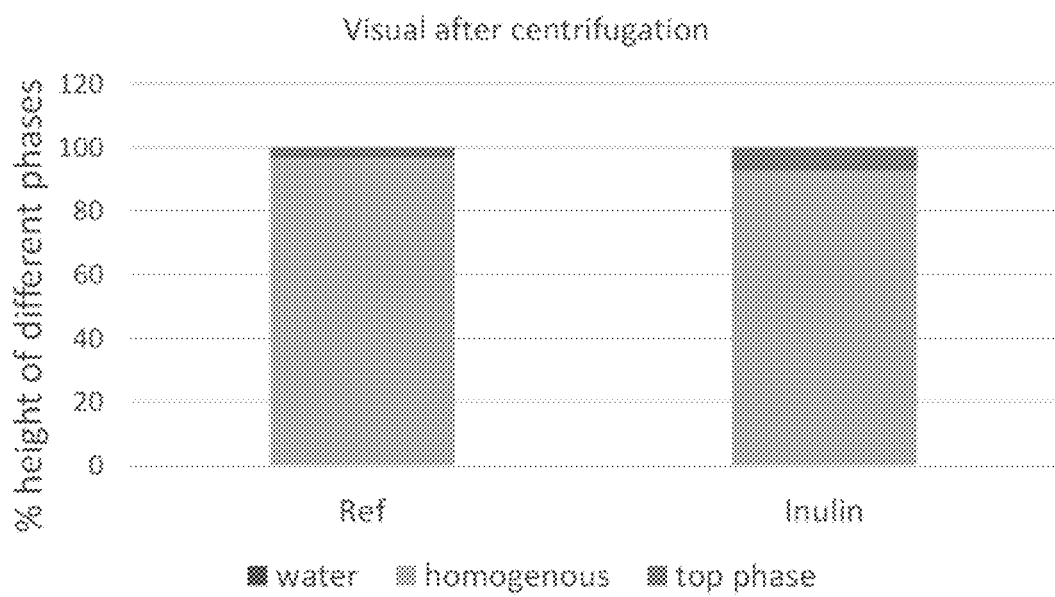
FIG. 11 represents the stability of the liquid cream with and without Inulin (Ref). The liquid cream is stable, either with maltodextrins or with inulin. The viscosity of the liquid cream with inulin is lower but acceptable. The stability of the liquid cream with Inulin is slightly lower but still acceptable (below 3% sediment).

The stability of the liquid cream with and without Inulin is represented in FIG. 11. The liquid cream is stable, either with maltodextrins or with inulin. The viscosity of the liquid cream with inulin is lower but acceptable. The stability of the liquid cream with Inulin is slightly lower but still acceptable (below 3% sediment).

Figure 12:
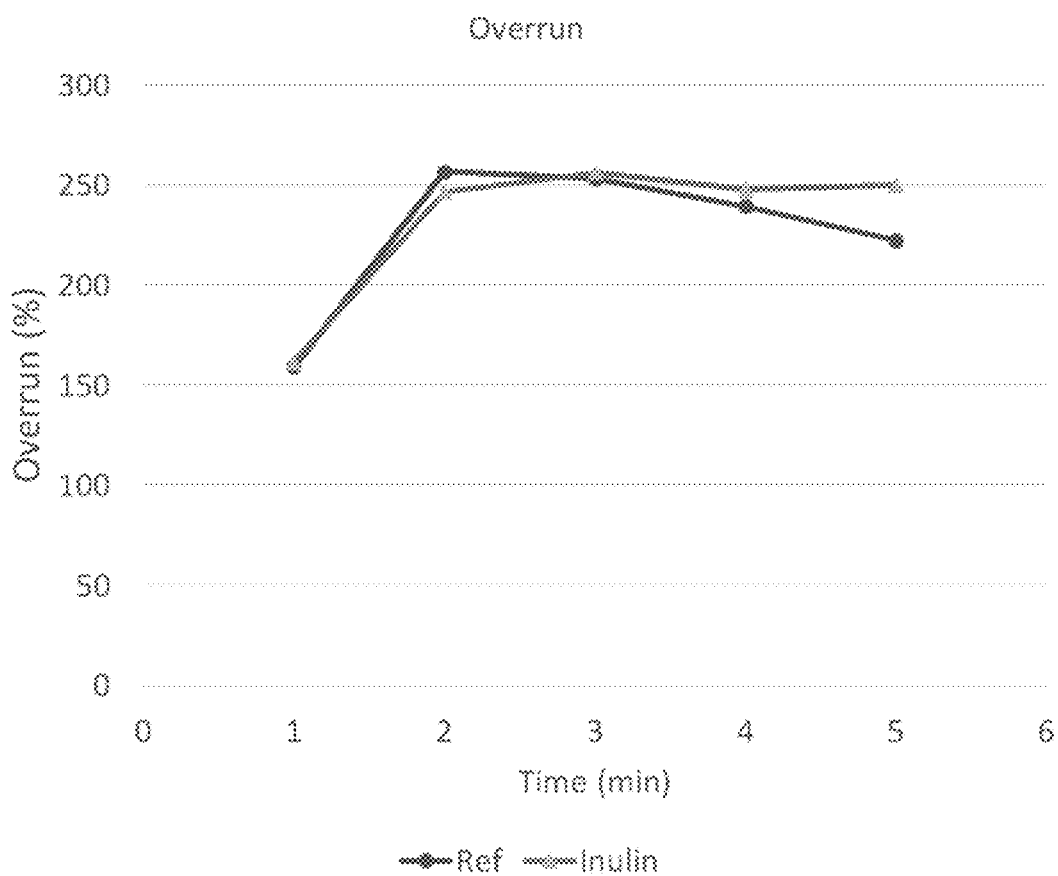
FIG. 12 represents the overrun of the whipped cream with and without Inulin (Ref). The overrun is comparable between whipped cream with maltodextrin and with Inulin.
Figure 13:
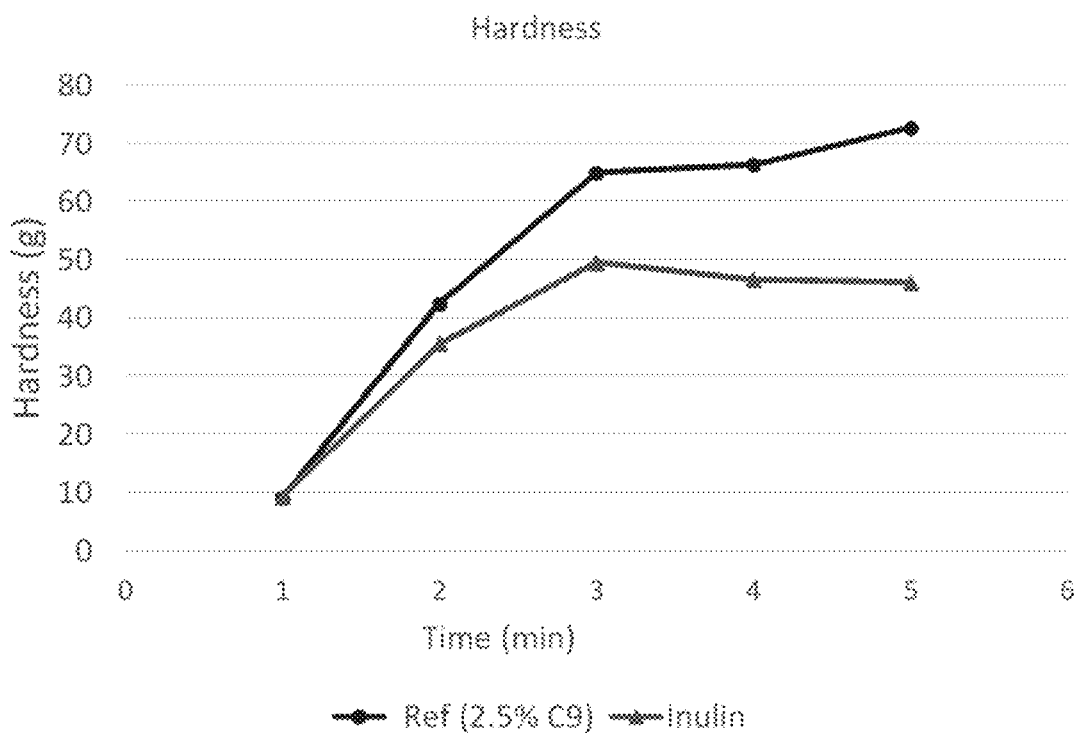
FIG. 13 represents the hardness of the foam of the whipped cream with and without Inulin (Ref).

Analysis of the Whipped Cream
Overrun
The overrun of the whipped cream with and without Inulin is represented in FIG. 12. The overrun is comparable between whipped cream with maltodextrin and with Inulin.
Hardness of the Foam
The hardness of the foam of the whipped cream with and without Inulin is represented in FIG. 13.
Taste

TABLE 19

| Ref P2.5 | +Inulin |
|---|---|
| Good texture, light vegetal taste | More foamy than ref but less compact, less vegetal taste and sweeter |

Ref P2.5: Pisane ™C9 at 2.5% (with maltodextrin) has been used as reference.

2.4.2.

2.4.3. Conclusion

The results with maltodextrin and with inulin are very similar.

Fibruline® Instant can replace maltodextrin in this application. The cream is less viscous, and the whipped cream is less textured, but the vegetal taste is reduced.

Example 3: Non-Dairy Culinary Cream 3.1 Reference Culinary Cream with 2.5% Pea Protein Isolate
All ingredients are listed in Table 20 (in g).
Preparation:
A blend is made with all dry ingredients and dispersed in water. Oil is added and mixed again. pH is adjusted to 7.0 with citric acid solution. The blend is heated at 60° C. while mixing (Ultraturax 1 min speed 4), further heated to 90° C. and kept for 30 seconds while mixing. The product is cooled to 20-25° C. while mixing and poured into sterile bottles in aseptic conditions.

TABLE 20

| Ingredients | In g |
|---|---|
| Water | 77.71 |
| Pea protein isolate (A)* | 2.50 |
| Sunflower oil | 16.50 |
| Fructose-glucose syrup | 2.30 |
| Thickener (E412-E415) | 0.28 |
| Monoglyceride | 0.20 |
| Sodium hexametaphosphate | 0.20 |
| Gellan gum | 0.10 |
| Sucrose ester | 0.10 |
| Carrageenan | 0.05 |
| Salt | 0.05 |
| Citric acid anhydrous | 0.01 |
| Total | 100 |

*(A): Pisane ™ C9

3.2 Culinary Cream with Different Concentrations of Pea Protein Pisane™ C9

All ingredients are listed in Table 21 (in g).

TABLE 21

| Ingredients | Comments | P1 | Ref P2.5% | P3 | P5 |
|---|---|---|---|---|---|
| Water | | 79.21 | 77.71 | 77.21 | 75.21 |
| Pea protein isolate | Pisane ™ C9 - Cosucra | 1.00 | 2.50 | 3.00 | 5.00 |
| Sunflower oil | | 16.50 | 16.50 | 16.50 | 16.50 |
| Fructose-glucose syrup | Fructomix F50/71% - Belgosuc | 2.30 | 2.30 | 2.30 | 2.30 |
| Thickener (E412-E415) | Lygomme MM 391 - Cargill | 0.28 | 0.28 | 0.28 | 0.28 |
| Monoglyceride | Myverol 18-04 K - Kerry | 0.20 | 0.20 | 0.20 | 0.20 |
| Sodium hexametaphosphate | SHMP FG MC - Prayon | 0.20 | 0.20 | 0.20 | 0.20 |
| Gellan gum | Kelcogel HS-B - CP Kelco | 0.01 | 0.01 | 0.01 | 0.01 |
| Sucrose ester | Sisterna SP70 - Siterna | 0.01 | 0.01 | 0.01 | 0.01 |
| Carrageenan | Lactarin MV 306 - FMC Biopolymer | 0.05 | 0.05 | 0.05 | 0.05 |
| Salt | | 0.05 | 0.05 | 0.05 | 0.05 |
| Citric acid anhydrous | Citric acid anhydrous BP 98 - AKtiva | 0.01 | 0.01 | 0.01 | 0.01 |
| TOTAL | | 100 | 100 | 100 | 100 |

Ref 2.5: Pisane ™C9 at 2.5% has been used as reference; P3 is a corresponding product comprising 3 wt. % Pisane ™ C9 and P5 is a corresponding product comprising 5 wt. % Pisane ™ C9.

Protocols:
Protocols are as described earlier.

3.2.1 Results

TABLE 22

| | P1 | Ref P2.5% | P3 | P5 |
|---|---|---|---|---|
| Visual aspect | Homogenous 100%, no foam | Homogenous 100%, no foam | Homogenous 100%, no foam | Homogenous 100%, no foam |
| pH | 6.88 | 7.14 | 7.22 | 6.8 |
| Viscosity (cps) | 440 | 504 | 512 | 1160 |
| Stability at 25° | | | | |
| Sediment (%) | 0 | 0 | 0 | 0 |
| Fat/top phase (%) | 0 | 0 | 0 | 0 |
| Homogeneous phase (%) | 100 | 100 | 100 | 100 |
| Water (%) | 0 | 0 | 0 | 0 |
| Stability at 72° + | | | | |
| Sediment (%) | 0 | 0 | 0 | 0 |
| Fat/top phase (%) | 0 | 0 | No data | No data |
| Homogeneous phase (%) | 43.4 | 42 | No data | No data |
| Water (%) | 56.60 | 58 | No data | No data |
| ΔE*ab | 4.19 | — | 0.86 | 6.11 |

TABLE 22-continued

|  | P1 | Ref P2.5% | P3 | P5 |
|---|---|---|---|---|
| Taste (25° C.) | Low vegetal taste, low astringency, smooth, creamy, liquid, white | Stronger vegetal taste, astringent, acid, slightly grey | Stronger vegetal taste, less astringent, sticky, yellowish | Very strong vegetal, astringent, viscous, fatty, rancid, yellowish |

Ref 2.5: Pisane™C9 at 2.5% has been used as reference; P3 is a corresponding product comprising 3 wt. % Pisane™ C9 and P5 is a corresponding product comprising 5 wt. % Pisane™ C9.
⁺ Heating in a water bath at 72° C. for 20 min

3.2.2 Conclusion

The viscosity of the culinary cream is optimal between 2.5 wt. % and 3 wt. % Pisane™ C9 (ie corresponding with between about 2.1 wt. % and 2.7 wt. % intact pea protein).

The concentration of Pisane™ C9 has no impact on the stability at 25° C. or at 72° C. Optimal taste is obtained with 2.5 wt. % Pisane™ C9, a compromise between vegetal taste, texture and creaminess.

Pisane™ C9 can be added in an amount from 1 wt. % to 3 wt. % in this application (i.e. corresponding with between about 0.80 wt. % and about 2.5 wt. % intact pea protein).

3.3 Non-Diary Culinary Cream Comprising Pulse Protein from Different Origin

All ingredients are listed in Table 23 (in g).

TABLE 23

| Ingredients | N1 | N3 | N5 | F1 | F3 | F5 |
|---|---|---|---|---|---|---|
| Water | 79.21 | 77.21 | 75.21 | 79.21 | 77.21 | 75.21 |
| Pea protein Isolate (B)* | 1.00 | 3.00 | 5.00 | — | — | — |
| Faba Bean protein Isolate (C)** | — | — | — | 1.00 | 3.00 | 5.00 |
| Sunflower oil | 16.50 | 16.50 | 16.50 | 16.50 | 16.50 | 16.50 |
| Fructose-glucose syrup | 2.30 | 2.30 | 2.30 | 2.30 | 2.30 | 2.30 |
| Thickener (E412-E415) | 0.28 | 0.28 | 0.28 | 0.28 | 0.28 | 0.28 |
| Monoglyceride | 0.20 | 0.20 | 0.20 | 0.20 | 0.20 | 0.20 |
| Sodium hexametaphosphate | 0.20 | 0.20 | 0.20 | 0.20 | 0.20 | 0.20 |
| Gellan gum | 0.10 | 0.10 | 0.10 | 0.10 | 0.10 | 0.10 |
| Sucrose ester | 0.10 | 0.10 | 0.10 | 0.10 | 0.10 | 0.10 |
| Carrageenan | 0.05 | 0.05 | 0.05 | 0.05 | 0.05 | 0.05 |
| Salt | 0.05 | 0.05 | 0.05 | 0.05 | 0.05 | 0.05 |
| Citric acid anhydrous | 0.01 | 0.01 | 0.01 | 0.01 | 0.01 | 0.01 |
| TOTAL | 100 | 100 | 100 | 100 | 100 | 100 |

*(B): Nutralys ® S85F-Roquette;
**(C): Faba bean protein isolate FBCP-90C-1709211 from Fenchem Protocols:
Protocols are as described earlier.

3.3.1 Results

TABLE 24

|  | N1 | N3 | N5 | F1 | F3 | F5 |
|---|---|---|---|---|---|---|
| Visual aspect | Stable 100%, no foam | Stable 100%, no foam | Stable 100%, no foam | Stable 100%, no foam | Stable 100%, | Stable 100%, |
| pH | 6.8 | 7.09 | 7.17 | 6.41 | 6.51 | 6.41 |
| Viscosity (cps) | 392 | 660 | 1210 | 432 | 790 | 1490 |
| Stability at 25° (%) |  |  |  |  |  |  |
| Sediment | 0 | 0 | 0 | 0 | 0 | 0 |
| Fat/top phase | 0 | 0 | 0 | 0 | 0 | 0 |
| Homogeneous phase (%) | 100 | 100 | 100 | 100 | 100 | 100 |
| Water | 0 | 0 | 0 | 0 | 0 | 0 |
| Stability at 72° (%)⁺ |  |  |  |  |  |  |
| Sediment | 0 | 0 | 0 | 18.75 | 35.29 | 0 |
| Fat/top phase | 0 | — | — | 0 | 0 | 0 |
| Intermediate | 44.44 | — | — | 56.25 | 29.41 | 68.28 |
| Water | 56.56 | — | — | 25.0 | 35.29 | 31.71 |
| ΔE*ab | 3.89 | 0.72 | 4.76 | 4.93 | 2.82 | 4.14 |

TABLE 24-continued

|  | N1 | N3 | N5 | F1 | F3 | F5 |
|---|---|---|---|---|---|---|
| Taste (25° C.) | Different vegetal taste, liquid, white | Cereal note astringent, bitter, grey | Strong vegetal taste, acid, rancid sticky, viscous | Better, vegetal taste, unpleasant, white | Viscous, very unpleasant, less bitter | Viscous, very unpleasant, toasted note, fatty, grey |

Pisane™ C9 at 2.5 wt. % has been used as reference for colour characterisation (see Table 22).
N1 represents the corresponding product comprising Nutralys ® at 1 wt. %, N2.5 represents the corresponding product with 2.5 wt. % Nutralys ®;
N5 represents the corresponding product with 5 wt. % Nutralys ®;
F1 represents the corresponding product with 1 wt. % Faba protein isolate;
F2.5 represents the corresponding product with 2.5 wt. % Faba protein isolate;
F5 represents the corresponding product with 5 wt. % Faba protein isolate.
⁺Heating in a water bath at 72° C.—20 min 3.3.1 Conclusion Pisane™ C9, Nutralys® S85F and *Faba* bean protein can be used in this application. The recommended dosage for the three protein isolates is the same, i.e. 2.5 wt. %.

Example 4: Non-Dairy Desert Cream 4.1 Reference Non-Dairy Dessert Cream with 3.9% Pea Protein All ingredients are listed in Table 25.

Preparation:

Pisane™ C9 is dispersed in the water with anti-lump helix and oil is added while mixing. Homogenisation is done with Ultaturrax for 2 min at speed 4. The solution is deaerated with Stephan (vacuum the solution at 3000 rpm), SHMP is added and the pH is adjusted to 6.70 with citric acid (50% solution). A blend is made with the rest of the dry ingredients. The blend is dispersed in the solution at 750 rpm and heated until 80° C. The blend is kept for 10 min at 80° C. while mixing and thereafter cooled down to 25° C. (while mixing) and poured into pots and stored at 4° C.

TABLE 25

| Ingredients | In g |
|---|---|
| Water | 77.89 |
| Crystal cane Sugar | 13.00 |
| Pea protein Isolate (A) | 3.90 |
| Modified starch | 2.50 |
| Sunflower oil | 1.60 |
| Carrageenan | 0.05 |
| Tricalcium phosphate anhydrous | 0.29 |
| Caramel colouring | 0.25 |
| Caramel flavour (N + NI) | 0.25 |
| Citric acid anhydrous | 0.07 |
| Sodium hexametaphosphate | 0.15 |
| Instant coffee | 0.05 |
| Total | 100 |

(A): Pisane ™ C9

4.2 Dessert Cream with Different Concentrations of Pea Protein Pisane™

All ingredients are listed in Table 26.

TABLE 26

| Ingredients | Comments | P1 | Ref 3.9% | P10 |
|---|---|---|---|---|
| Water |  | 80.94 | 78.04 | 71.94 |
| Pea protein isolate | Pisane ™ C9 Cosucra | 1.00 | 3.90 | 10.00 |
| Crystal cane Sugar |  | 13.00 | 13.00 | 13.00 |
| Modified starch | C*Hiform A 12747 | 2.50 | 2.50 | 2.50 |
| Sunflower oil |  | 1.60 | 1.60 | 1.60 |
| Tricalcium phosphate anhydrous | Prayphos TCP 308 FG-Prayon | 0.29 | 0.29 | 0.29 |
| Caramel colouring | WO 170 - Nigay | 0.25 | 0.25 | 0.25 |
| Sodium hexametaphosphate | SHMP - Prayon | 0.15 | 0.15 | 0.15 |
| Caramel flavour (N + NI) | Caramel supercaps DF20368 - Givaudan | 0.10 | 0.10 | 0.10 |
| Instant coffee |  | 0.05 | 0.05 | 0.05 |
| Carrageenan | Lactocel FC 3263 - FMC Biopolymer | 0.05 | 0.05 | 0.05 |
| Citric acid anhydrous | Citric acid anhydrous BP 98 - Aktiva | 0.07 | 0.07 | 0.07 |
| Total |  | 100 | 100 | 100 |

Ref 3.9% is the reference product comprising Pisane ™ C9, at 3.9 wt. %. P1 and P10 are corresponding products that respectively comprise 1 and 10 wt. % Pisane ™ C9.

Protocols: Protocols are as described earlier.

4.2.1 Results

TABLE 27

|  | P1 | Ref 3.9% | P10 |
|---|---|---|---|
| Comment on process | Very liquid after cooling | Texture ok | Very thick texture after cooling |

TABLE 27-continued

|  | P1 | Ref 3.9% | P10 |
|---|---|---|---|
| pH | 6.72 | 6.8 | 6.82 |
| Texture (g) | 6.48 | 59.40 | 449.39 |
| Stability (%) | 54 | 100 | 100 |
| ΔE*ab | 6.83 | — | 1.12 |
| Taste | Texture very liquid, taste sweeter with more coffee/caramel taste | Texture ok, taste ok (slightly vegetal) | Too textured, taste vegetal but still acceptable |

Ref 3.9% is the reference product comprising Pisane ™ C9, at 3.9 wt. %. P1 and P10 are corresponding products that respectively comprise 1 and 10 wt. % Pisane ™ C9.

4.2.2. Conclusion

In this application, Pisane™ C9 is necessary for the stability of the product. The concentration in protein is correlated to the viscosity. Between 3.9% and 10% Pisane™ C9 can be used in this application (i.e. corresponding with between about 3.0 wt. % and about 9.0 wt. % intact pea protein).

4.3 Non-Dairy Dessert Cream Comprising Pulse Protein from Different Origin

All ingredients are listed in Table 28.

TABLE 28

| Ingredients | N1 | N3 | N5 | N10 | F1 | F3 | F5 | F10 |
|---|---|---|---|---|---|---|---|---|
| Water | | | | up to 100% | | | | |
| Pea protein Isolate (B) | 1.00 | 3.9 | 5.00 | 10.00 | — | — | — | — |
| Faba Bean protein Isolate (C) | — | — | — | — | 1.00 | 3.00 | 5.00 | 10.00 |
| Crystal cane Sugar | 13.00 | 13.00 | 13.00 | 13.00 | 13.00 | 13.00 | 13.00 | 13.00 |
| Modified starch | 2.50 | 2.50 | 2.50 | 2.50 | 2.50 | 2.50 | 2.50 | 2.50 |
| Sunflower oil | 1.60 | 1.60 | 1.60 | 1.60 | 1.60 | 1.60 | 1.60 | 1.60 |
| Tricalcium phosphate anhydrous | 0.29 | 0.29 | 0.29 | 0.29 | 0.29 | 0.29 | 0.29 | 0.29 |
| Caramel colouring | 0.25 | 0.25 | 0.25 | 0.25 | 0.25 | 0.25 | 0.25 | 0.25 |
| Sodium hexametaphosphate | 0.15 | 0.15 | 0.15 | 0.15 | 0.15 | 0.15 | 0.15 | 0.15 |
| Caramel flavour (N + NI) | 0.10 | 0.10 | 0.10 | 0.10 | 0.10 | 0.10 | 0.10 | 0.10 |
| Instant coffee | 0.05 | 0.05 | 0.05 | 0.05 | 0.05 | 0.05 | 0.05 | 0.05 |
| Carrageenan | 0.05 | 0.05 | 0.05 | 0.05 | 0.05 | 0.05 | 0.05 | 0.05 |
| Citric acid anhydrous | 0.07 | 0.07 | 0.07 | 0.07 | 0.07 | 0.07 | 0.07 | 0.07 |
| TOTAL | 100 | 100 | 100 | 100 | 100 | 100 | 100 | 100 |

(B): Nutralys ® S85F-Roquette;
(C): Faba bean protein isolate FBCP-90C-1709211 from Fenchem Protocols:

Protocols are as described earlier.

4.3.1 Results

TABLE 29 A

|  | N1 | N3 | N5 | N10 |
|---|---|---|---|---|
| Comment on process | Very liquid texture after cooling | Texture ok | thick texture after cooling | Very thick texture after cooling |
| pH | 5.97 | 5.37 | 6.21 | 5.86 |
| Texture (g) | 8.12 | 54.39 | 87.91 | 730.49 |
| Stability (%) | 44.23 | 95 | 98.75 | 100 |
| ΔE*ab | 8.21 | 3.99 | 4.76 | 4.71 |
| Taste | Texture not acceptable, very liquid and sandy | Taste strong vegetal, not creamy, sandy, more sweet, acceptable | Sandy, astringent, more sweet, acceptable | Astringent, piquant, bitter, sandy, very thick texture |

Pisane ™ C9 at 3.9 wt. % has been used as reference (see Table 27)

TABLE 29 B

|  | F1 | F3 | F5 | F10 |
|---|---|---|---|---|
| Comment on process | Very liquid texture after cooling | Liquid texture after cooling | Texture ok | Very thick texture after cooloing |

TABLE 29 B-continued

|  | F1 | F3 | F5 | F10 |
|---|---|---|---|---|
| pH | 5.95 | 5.34 | 6.06 | 5.37 |
| Texture (g) | 5.12 | 18.4 | 48.72 | 615.37 |
| Stability (%) | 34 | 78.46 | 97.59 | 100 |
| ΔE*ab* | 9.55 | 5.25 | 3.07 | 2.50 |
| Taste | Sandy, piquant, bitter, taste unpleasant, texture, liquid | Acid, taste unpleasant, texture too liquid | Sandy, acid, taste unpleasant, texture almost like the ref P3.9*** | Very thick texture, sandy, unpleasant taste |

P3.9 = Pisane ™ C9 (3.9 wt. %) has been used as reference (see Table 27)

4.3.2 Conclusion

Pisane™ C9, Nutralys®S85F and *Faba* bean protein can be used in this application. The recommended dosage is between 3.9 wt. % and 10 wt. % for Pisane™ C9 and for the Nutralys® S85F and between 5 wt. % and 10 wt. % for *Faba* bean protein. Stability is a little bit lower than Pisane™ C9. Taste is strongly vegetal from 3%. *Faba* bean protein brings more vegetal notes and unpleasant off notes. The taste can be improved by flavouring.

4.4 Non-Dairy Dessert Cream Comprising Inulin

All ingredients are listed in Table 30.

TABLE 30

| Ingredients | In g |
|---|---|
| Water | 81.07 |
| Spray-dried maltodextrin (18DE) | 6.0 |
| Pea protein Isolate (A) | 4.7 |
| Desugared inulin | 3.00 |
| Modified starch | 2.60 |
| Sunflower oil | 2.00 |
| Carrageenan | 0.04 |
| Tricalcium phosphate anhydrous | 0.28 |
| Vanilla flavour | 0.3 |
| Sucralose | 0.015 |
| Total | 100 |

Example 5: Non-Dairy Frozen Dessert 5.1 Reference Non-Dairy Frozen Dessert with 2% Pea Protein All ingredients are listed in Table 31.

Preparation:

The dry ingredients are blended together. The dry blend, the glucose syrup and the melted fat are added to water at 45-50° C. All is homogenized at 60° C. and 180 bars, and pasteurized on a plate heat exchanger at 85° C. for 30 seconds, and thereafter cooled down to 5° C. The liquid mix is aged for 18 hours at 5° C. with intermediate agitation and thereafter freezed in a continuous freezer. The resulting ice cream is filled into pots and stored at −20° C.

TABLE 31

| Ingredients | In g |
|---|---|
| Water | 64.40 |
| Pea protein Isolate (A)* | 2.00 |
| Crystal sugar | 13.00 |
| Vegetable fat (coprah) | 8.00 |
| Glucose syrup 38 DE | 6.00 |
| Emulsifier & stabiliser system[1] | 0.50 |
| Spray-dried maltodextrin (18 DE) | 6.00 |
| Vanilla bourbon flavour | 0.10 |
| Total | 100 |

*(A): Pisane ™ C9.
2 wt. % Pisane ® C9 corresponds with about 1.60 to 1.7 wt. % pea protein.

5.2 Non-Dairy Frozen Dessert with Different Concentrations Pea Protein Pisane™ C9

All ingredients are listed in Table 32.

TABLE 32

| Ingredients | Comments | P0.6 | P1.22 | P1.83 | P2.44 | P3.44 | P3.66 |
|---|---|---|---|---|---|---|---|
| Water |  | 63.60 | 62.98 | 62.37 | 61.76 | 61.15 | 60.54 |
| Pea protein isolate | Pisane ™ C9 | 0.60 | 1.22 | 1.83 | 2.44 | 3.05 | 3.66 |
| Crystal sugar |  | 13.00 | 13.00 | 13.00 | 13.00 | 13.00 | 13.00 |
| Vegetable fat (coprah) | Ertilor 024/26-Fuji Oil Europe | 10.00 | 10.00 | 10.00 | 10.00 | 10.00 | 10.00 |
| Glucose syrup 38 DE | Belgogluc HM 70-81-Belgogluc | 6.00 | 6.00 | 6.00 | 6.00 | 6.00 | 6.00 |
| Emulsifier & stabiliser system[1] | Cremodan SE 30-Danisco | 0.50 | 0.50 | 0.50 | 0.50 | 0.50 | 0.50 |
| Spray-dried maltodextrin (18 DE) | C*Dry MD 01915 | 6.00 | 6.00 | 6.00 | 6.00 | 6.00 | 6.00 |
| Vanilla flavour |  | 0.30 | 0.30 | 0.30 | 0.30 | 0.30 | 0.30 |
| TOTAL |  | 100 | 100 | 100 | 100 | 100 | 100 |

Protocols:
Protocols are as described earlier.

5.2.1 Results

TABLE 33

|  | P0.6 | P1.22 | P1.83 | P2.44 | P3.44 | P3.66 |
|---|---|---|---|---|---|---|
| Viscosity of the mix (cps), | 208 | 440 | 680 | 1200 | 3200 | 3840 |
| Speed of melting after 2 h (%) | 68.6 | 71.4 | 70 | 69.2 | 66 | 67.6 |
| Viscosity of the melting (cps) | 320 | 1160 | 2080 | 2800 | 3280 | 3840 |
| Stability of the melting (%) | 65 | 100 | 100 | 100 | 100 | 100 |
| Taste | Aqueous, crystals, not sweet enough, seems like water ice cream | More creamy but not enough | Texture ok, good creaminess | More creamy but also more vegetal | More creamy and vegetal | Too vegetal |

Hardness

Figure 14:
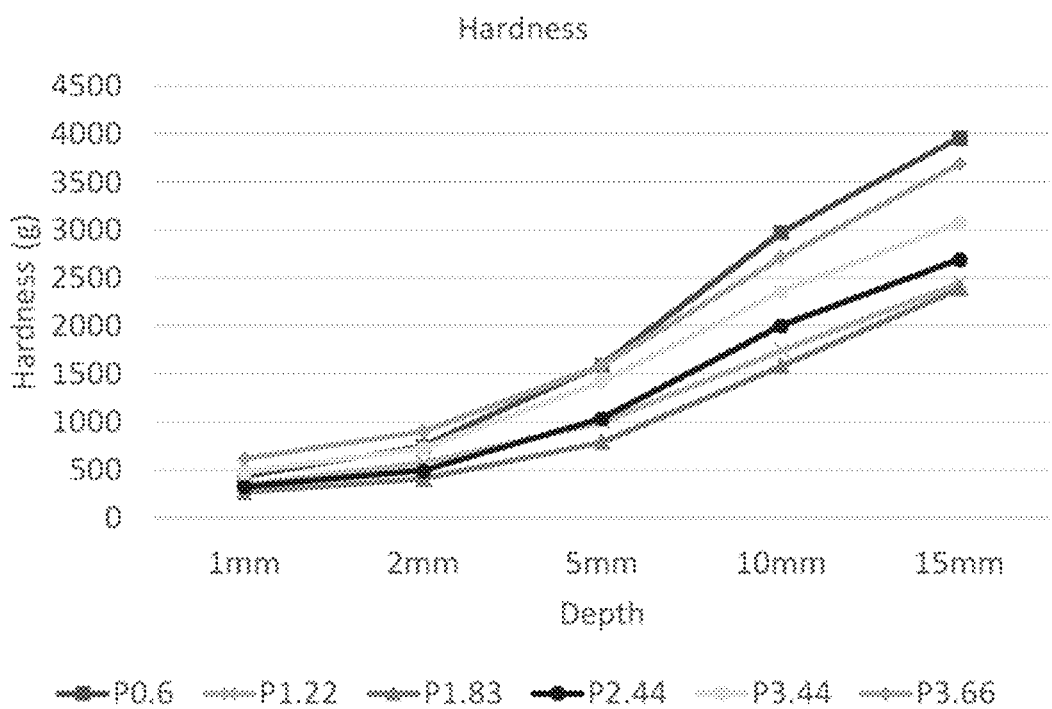
FIG. 14 shows the hardness of the frozen dessert as a function of the depth at different Pisane™ C9 concentrations.

FIG. 14 shows the hardness in function of the depth at different Pisane™ C9 concentrations.

5.2.2 Conclusion

In this application, Pisane™ C9 is necessary for the stability of the melting and the creaminess of the ice cream. Pisane™ C9 affects the viscosity of the mix and of the melting as well as the hardness of the ice cream. Between 1.2% and 3% Pisane can be used in this application. At higher concentration, the high viscosity of the frozen dessert could become a technical challenge.

5.3 Comparison between non-dairy frozen dessert comprising pulse protein from different origin All ingredients are listed in Table 34.

TABLE 34

| Ingredients | P2*** | N1 | N4 | F1 | F2 | F3 | F4 | F5 |
|---|---|---|---|---|---|---|---|---|
| Water | 64.40 | 65.40 | 62.40 | 65.40 | 64.40 | 63.40 | 62.40 | 61.40 |
| Pea protein isolate (A) | 2.00 | | | | | | | |
| Pea protein isolate (B) | | 1.00 | 4.00 | | | | | |
| Faba bean protein isolate (C) | | | | 1.00 | 2.00 | 3.00 | 4.00 | 5.00 |
| Crystal sugar | 13.00 | 13.00 | 13.00 | 13.00 | 13.00 | 13.00 | 13.00 | 13.00 |
| Vegetable fat (coprah) | 8.00 | 8.00 | 8.00 | 8.00 | 8.00 | 8.00 | 8.00 | 8.00 |
| Glucose syrup 38 DE | 6.00 | 6.00 | 6.00 | 6.00 | 6.00 | 6.00 | 6.00 | 6.00 |
| Emulsifier & stabiliser system[1] | 0.50 | 0.50 | 0.50 | 0.50 | 0.50 | 0.50 | 0.50 | 0.50 |
| Spray-dried maltodextrin (18 DE) | 6.00 | 6.00 | 6.00 | 6.00 | 6.00 | 6.00 | 6.00 | 6.00 |
| Vanilla bourbon flavour | 0.10 | 0.10 | 0.10 | 0.10 | 0.10 | 0.10 | 0.10 | 0.10 |
| Total | 100 | 100 | 100 | 100 | 100 | 100 | 100 | 100 |

(A): Pisane ™ C9-Cosucra;
(B): Nutralys ® S85F-Roquette;
(C): Faba bean protein isolate FBCP-90C-1709211 from Fenchem Protocols:
Protocols are as described earlier.

5.3.1 Results

TABLE 35 A

|  | P2*** | N1 | N4 |
|---|---|---|---|
| Viscosity of the mix (cps) | 600 | 170 | 2320 |
| Comment on melting | Homogenous | homogenous but not stable | Homogenous |
| Speed of melting after 2 h (%) | 77.5 | 81.7 | 81.4 |
| pH | 7.42 | 7.45 | 7.43 |

TABLE 35 A-continued

|  | P2*** | N1 | N4 |
|---|---|---|---|
| Viscosity of the melting(cps) | 1260 | 200 | 5600 |
| Stability of the melting (%) | 100 | 70 | 100 |
| ΔE*ab | — | 1.53 | 5.50 |
| Taste | Classic, creamy slightly vegetal | More sweet taste, less vanilla, aqueous | Less aqueous, creamier, more vegetal, (colour more orange) |

***P2 has been used as reference and comprises 2 wt. % Pisane ™ C9

TABLE 35 B

|  | F1 | F2 | F3 | F4 | F5 |
|---|---|---|---|---|---|
| Viscosity of the mix (cps) | 135 | 200 | 300 | 530 | 860 |
| Comment on melting | homogenous but not stable | homogenous but not stable | homogenous but not stable | homogenous (limit stable) | homogenous |
| Speed of melting after 2 h (%) | 79.4 | 77.7 | 72.9 | 84.9 | 81.9 |
| pH | 6.97 | 6.79 | 6.67 | 6.59 | 6.53 |
| Viscosity of the melting(cps) | 180 | 300 | 450 | 1960 | 2560 |
| Stability of the melting (%) | 70 | 67 | 63 | 100 | 100 |
| ΔE*ab | 2.80 | 2.33 | 2.63 | 2.19 | 4.01 |
| Taste | Aqueous with faba bean vegetal taste, | Aqueous, more faba bean vegetal taste, not vanilla | Creamier, still more faba bean vegetal taste, almond/marzipan note | Creamy, strong almond/marzipan taste, faba bean vegetal note | Creamy, strong almond/marzipan taste, faba bean vegetal note |

P2 has been used as reference for colour characterisation

Hardness

Figure 15:
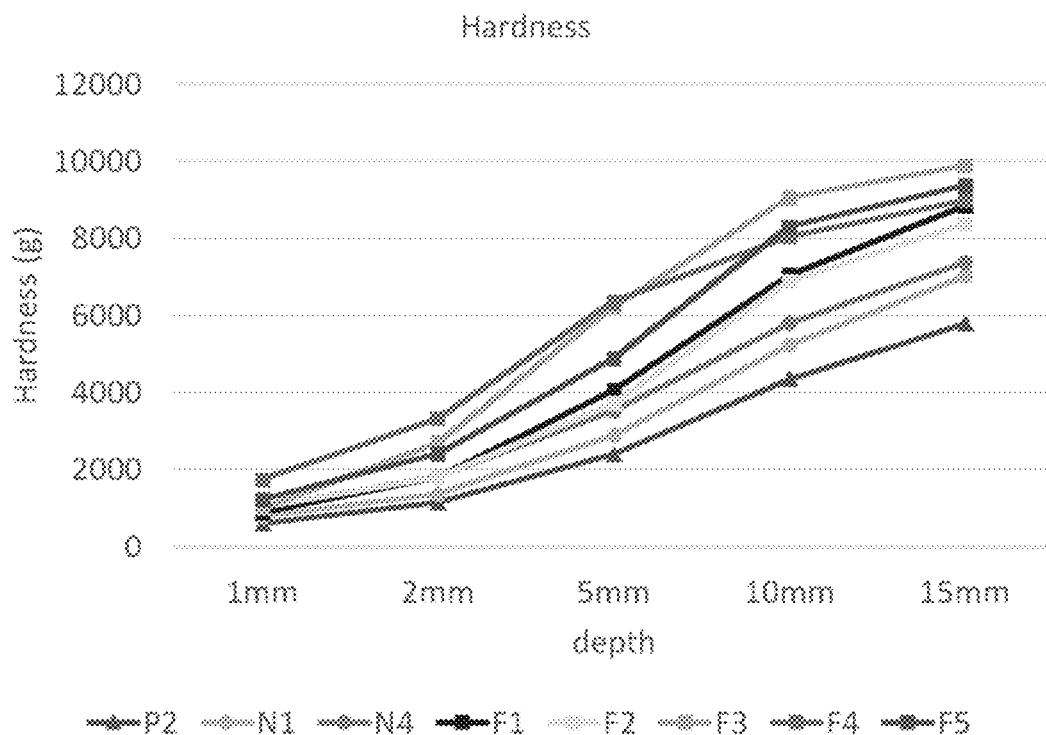
FIG. 15 shows the hardness of the frozen dessert in function of the depth at different protein concentrations (Pisane™ C9 (P2), Nutralus® S85F (N1, N4) and Faba bean protein (F1, F2, F3, F4, F5)).

FIG. 15 shows the hardness of the frozen dessert in function of the depth at different protein concentrations.

5.3.2 Conclusion

Pisane™ C9, Nutralys® S85F and *faba* bean protein Fenchem can be used in this application. The recommended dosage is higher than 1 wt. % and can be increased up to 5 wt. %. (corresponding with between about 0.8 wt % and 4.5 wt. % intact pea protein for Pisane™ C9). *Faba* bean brings more vegetal and marzipan notes. Formulation can be adapted to adapt the taste (flavouring).

5.4 Addition of Inulin to the frozen dessert at different concentrations

All ingredients are listed in Table 36.

TABLE 36

| Ingredients | P2*** | I3 | I5 | I10 |
|---|---|---|---|---|
| Water | 64.40 | 61.40 | 59.40 | 54.40 |
| Pisane ™ C9 | 2.00 | 2.00 | 2.00 | 2.00 |
| Fibruline ® Instant | — | 3.00 | 5.00 | 10.00 |
| Crystal sugar | 13.00 | 13.00 | 13.00 | 13.00 |
| Vegetable fat (coprah) | 8.00 | 8.00 | 8.00 | 8.00 |
| Glucose syrup 38 DE | 6.00 | 6.00 | 6.00 | 6.00 |
| Emulsifier & stabiliser system [1] | 0.50 | 0.50 | 0.50 | 0.50 |
| Spray-dried maltodextrin (18 DE) | 6.00 | 6.00 | 6.00 | 6.00 |
| Vanilla bourbon flavour | 0.10 | 0.10 | 0.10 | 0.10 |
| Total | 100 | 100 | 100 | 100 |

***P2 has been used as reference and comprises 2 wt. % Pisane ™ C9

5.4.1 Results

TABLE 37

|  | P2*** | I3 | I5 | I10 |
|---|---|---|---|---|
| Viscosity of the mix (cps) | 600 | 580 | 880 | 980 |
| Comment on melting | homogenous | homogenous | Homogenous | Homogenous |
| pH | 7.42 | 7.38 | 7.44 | 7.44 |
| Viscosity of the melting (cps) | 1260 | 1300 | 2080 | 2400 |
| Stability of the melting (%) | 100 | 100 | 100 | 100 |
| ΔE*ab | — | 0.24 | 0.12 | 0.93 |

TABLE 37-continued

|  | P2*** | I3 | I5 | I10 |
|---|---|---|---|---|
| Taste | Classic, creamy slightly vegetal | A little bit creamier than P2 | Very nice mouthfeel and creaminess | very creamy |

***P2 has been used as reference for colour characterisation

Hardness

Figure 16:
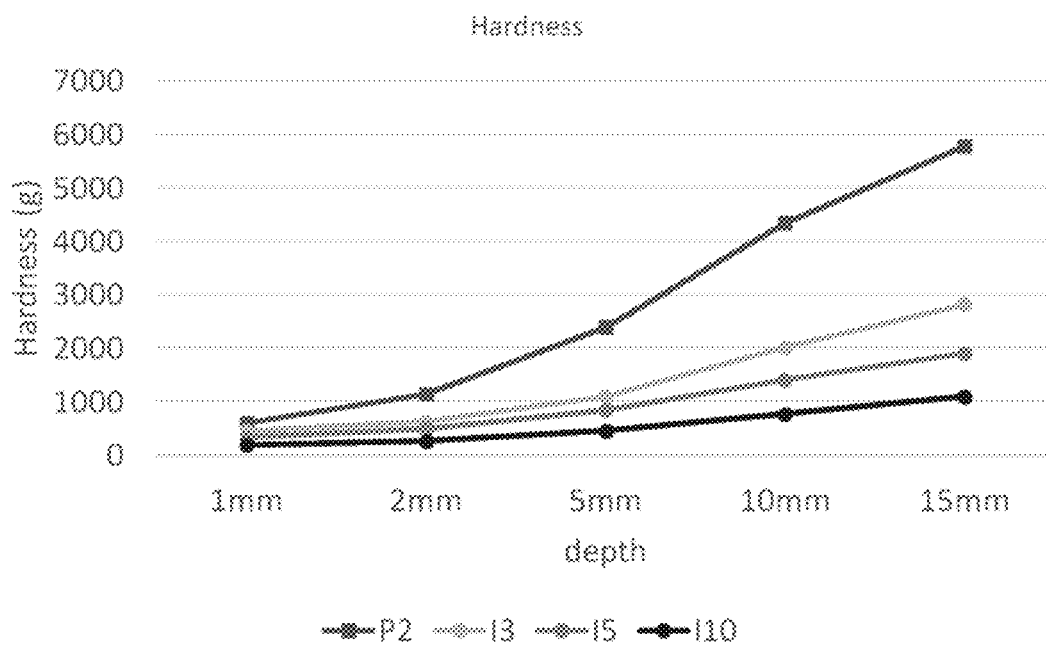
FIG. 16 shows the hardness of the ice cream in function of the depth at different Inulin concentrations (P2, I 3, I 5, I 10).
Figure 17:
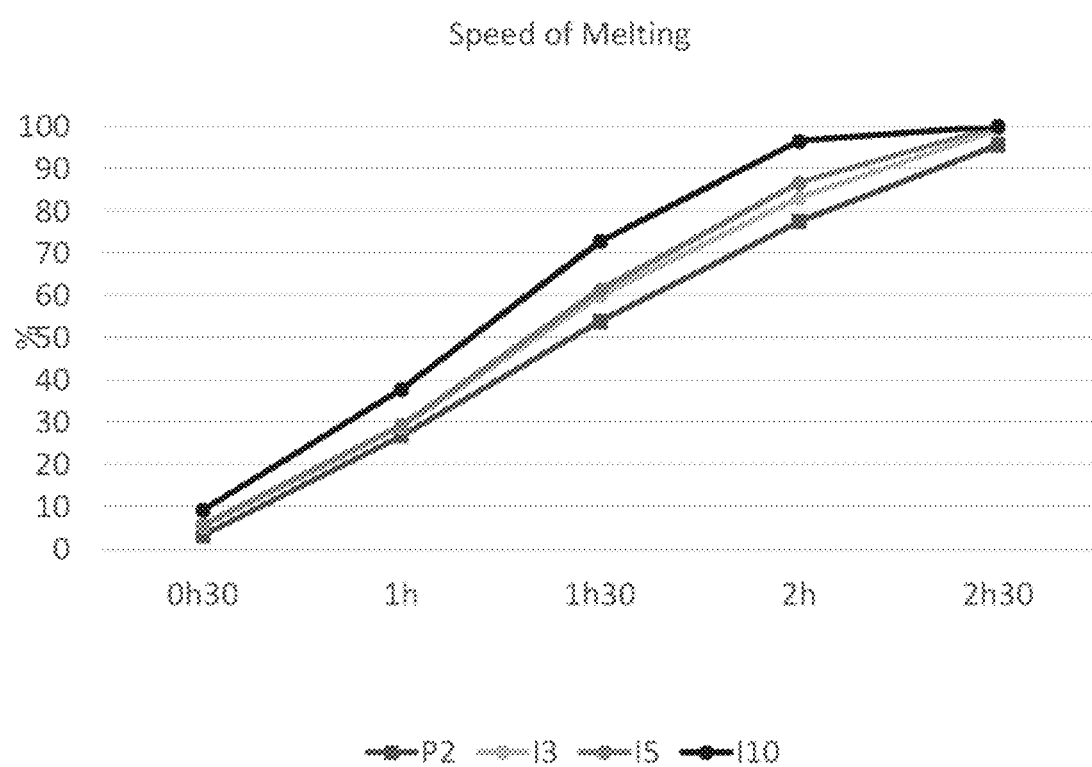
FIG. 17 shows the melting rate of the ice cream at different Inulin concentrations (P2, I 3, I 5, I 10).

FIG. 16 shows the hardness of the ice cream in function of the depth at different Inulin concentrations Melting Rate FIG. 17 shows the melting rate of the ice cream at different Inulin concentrations 5.4.2 Conclusion Fibruline® Instant can be used in this application. It reduces the hardness of the cream with moderate increase of the viscosity of the ice cream. Inulin brings also creaminess and reduces the ice crystal formation.

The invention claimed is:

1. A cream substitute comprising non-hydrolysed pulse protein in an amount comprised between 0.5 wt. % and 10 wt. % based on the total weight of the cream substitute and a soluble fiber in an amount between 0.5 wt. % and 5 wt. % based on the total weight of the cream substitute, wherein said soluble fiber is selected from inulin, glucooligosaccharides (GOSs), isomaltooligosaccharides (IMOs), galactooligosaccharides (TOSs), pyrodextrins, polydextrose, branched maltodextrins, indigestible dextrins and soluble oligosaccharides derived from oleaginous plants or protein-producing plants, or combinations thereof, and wherein the degree of hydrolysis of the pulse protein is less than 5% and wherein said cream substitute contains less than 1 wt. % of dairy-derived ingredients based on the total weight of the cream substitute.

2. The cream substitute according to claim 1, wherein the cream substitute comprises pulse protein derived from pulses selected from the group comprising lentils, beans, peas, chickpeas and combinations thereof.

3. The cream substitute according to claim 1, wherein said pulse protein is the main protein present in the cream substitute and wherein said cream substitute may comprise other proteins selected from caseinate, casein, whey, soy, oat, coconut, rice, gluten, nut, wheat and almonds, and wherein the total amount of non-pulse protein is lower than the amount of pulse protein.

4. The cream substitute according to claim 1, wherein the pulse protein is the sole source of vegetable protein.

5. The cream substitute according to claim 1, wherein the pulse protein is pea protein.

6. The cream substitute according to claim 1, wherein the pulse protein is *faba* bean protein.

7. A cream substitute according to claim 1, wherein said cream substitute is chosen from: an ice cream, a whipped cream, a culinary cream, or a milk dessert substitute, preferably a milk dessert substitute made without lactic ferments.

8. The cream substitute according to claim 7, wherein said cream substitute is an ice cream comprising:
sugar in an amount of from 0 wt. % to 20 wt. %,
glucose and/or dextrose and/or fructose in an amount of from 0 wt. % to 20 wt. %,
vegetable fat in an amount of from 1.5 wt. % to 5 wt. %, and optionally
additives selected from: flavours, colorants, stabilisers, thickeners, gelling agents, emulsifiers, bulking agent in an amount of from 0.05 wt. % to 10 wt. %,
and wherein said wt. % are calculated based on the total weight of the ice cream.

9. The cream substitute according to claim 8 wherein the amount of non-hydrolysed pulse protein is between 1.0 wt. % and 5.0 wt. %.

10. The cream substitute according to claim 2, wherein the beans are *faba* beans.

11. The cream substitute according to claim 1, wherein the pulse protein is the sole source of protein.

12. The cream substitute according to claim 1, wherein the pulse protein is a pea protein isolate.

13. The cream substitute according to claim 1, wherein the pulse protein is a *faba* bean protein isolate.

14. The cream substitute according to claim 1, wherein the cream substitute is in liquid form.

15. A cream substitute comprising:
non-hydrolysed pulse protein in an amount comprised between 0.5 wt. % and 10 wt. %, wherein the degree of hydrolysis of the pulse protein is less than 5%,
a soluble fiber in an amount comprised between 0.5 wt. % and 5 wt. %, wherein said soluble fiber is selected from inulin, glucooligosaccharides (GOSs), isomaltooligosaccharides (IMOs), galactooligosaccharides (TOSs), pyrodextrins, polydextrose, branched maltodextrins, indigestible dextrins and soluble oligosaccharides derived from oleaginous plants or protein-producing plants, or combinations thereof, and
at least one further protein selected from caseinate, casein, whey, soy, oat, coconut, rice, gluten, nut, wheat and almonds, and wherein the total amount of proteins, other than pulse protein, is lower than the amount of pulse protein,
wherein said cream substitute contains less than 1 wt. % of dairy-derived ingredients, and
wherein said wt. % are calculated based on the total weight of the cream substitute.

* * * * *